United States Patent
Hutchings et al.

(10) Patent No.: US 6,384,035 B1
(45) Date of Patent: *May 7, 2002

(54) HETEROCYCLES USEFUL IN THE TREATMENT OF BENIGN PROSTATIC HYPERPLASIA

(75) Inventors: Richard H. Hutchings, Ann Arbor, MI (US); Haripada Khatuya, San Diego, CA (US); Gee-Hong Kuo, Scotch Plains, NJ (US); Xiaobing Li, San Diego, CA (US); William V. Murray, Belle Mead, NJ (US); Catherine Prouty, Doylestown, PA (US); Frank Villani, Perkasie, PA (US); Nelson C. F. Yim, Ambler, PA (US); Cynthia Maryanoff, Forest Grove, PA (US)

(73) Assignee: Ortho-McNeil Pharmaceutical, Inc., Raritan, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/169,571

(22) Filed: Oct. 9, 1998

Related U.S. Application Data

(60) Provisional application No. 60/061,618, filed on Oct. 9, 1997.

(51) Int. Cl.[7] .................. A01N 43/00; A01N 43/58; C07D 205/08; C07D 405/00; C07D 241/04

(52) U.S. Cl. .................. 514/252.13; 514/210.02; 514/210.2; 514/211.03; 514/211.15; 514/212.08; 514/217.05; 514/217.06; 514/252.14; 514/253.09; 514/253.1; 514/254.02; 514/254.05; 540/200; 540/356; 540/362; 540/451; 540/463; 540/524; 540/598; 540/601; 544/364; 544/365; 544/366; 544/367; 544/369; 544/370; 544/371; 544/372; 544/379; 544/295; 544/360

(58) Field of Search .................. 514/210, 212, 514/252, 210.02, 210.2, 211.03, 211.15, 212.08, 217.05, 217.06, 252.13, 252.14, 253.09, 253.1, 254.02, 254.05; 540/362, 356, 451, 463, 524; 544/295, 362, 366, 379, 395, 360, 365, 367, 392, 364, 369, 370, 371, 372

(56) References Cited

U.S. PATENT DOCUMENTS

| | | | |
|---|---|---|---|
| 5,332,732 A | 7/1994 | Scott et al. | 514/212 |
| 5,403,847 A | 4/1995 | Gluchowski et al. | 514/318 |
| 5,605,896 A | 2/1997 | Leonardi et al. | 514/218 |

FOREIGN PATENT DOCUMENTS

EP  0 416 841 A2  3/1991

OTHER PUBLICATIONS

Scott M.K. et al. (1995) Piperazinylalkyl Heterocycles as Potential Antipsychotic Agents. Journal of Medicinal Chemistry. vol. 38, No. 21: 4198–4210.

Reitz A. B. et al. (1995) N–Aryl–N–Benzylpiperazines as Potential Antipsychotic Agents. Journal of Medicinal Chemistry. vol. 38, No. 21: 4211–4222.

Reitz A. B. et al. (1994) A New Arylpiperazine Antipsychotic with High D2/D3/5–HT1A/∞1A–Adrenergic Affinity and A Low Potential for Extrapyramidal Effects. vol. 37, No. 8: 1060–1062.

PCT International Search Report of PCT/US 98/21470.

Breslin D, Fields DW, Chou T–C, Marion DN, Kane M, Vaughan ED, and Felsen D (1993) Medical management of benign prostatic hyperplasia: a canine model comparing the in vivo efficacy of alpha–1 adrenergic antagonists in the prostate. J. Urol. 149: 395–399.

Bruno JF, Whittaker J, Song J, and Berelowitz M. (1991) Molecular cloning and sequencing of a cDNA encoding a human α1A adrenergic receptor. Biochem. Biophys. Res. Commun. 179: 1485–1490.

Bylund D.B, Eikenberg DC, Hieble JP, Langer SZ, Lefkowitz RJ, Minneman KP, Molinoff PB, Ruffolo RR, and Trendelenburg U (1994) IV. International Union of Pharmacology nomenclature of adrenoceptors. Pharmacol. Rev. 46: 121–136.

Carruthers SG (1994) Adverse effects of α1–adrenergic blocking drugs. Drug Safety 11: 12–20.

Faure C, Gouhier C, Langer SZ, and Graham D (1995) Quantification of α1–adrenoceptor subtypes in human tissues by competitive RT–PCR analysis. Biochem. Biophys. Res. Commun. 213: 935–943.

Flavahan NA and VanHoutte PM (1986) α1–Adrenoceptor subclassification in vascular smooth muscle. Trends Pharmacol. Sci. 7: 347–349.

(List continued on next page.)

Primary Examiner—Richard L. Raymond
(74) Attorney, Agent, or Firm—Ruby Hope

(57) ABSTRACT

This invention relates a to a series of heterocyclic substituted piperazines of Formula I

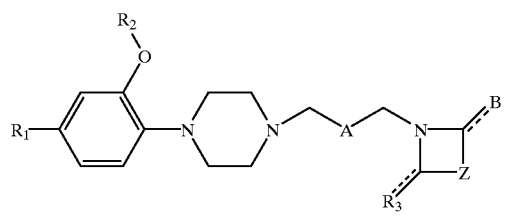

pharmaceutical compositions containing them and intermediates used in their manufacture. The compounds of the invention selectively inhibit binding to the α-1a adrenergic receptor, a receptor which has been implicated in benign prostatic hyperplasia. As such the compounds are potentially useful in the treatment of this disease.

12 Claims, 1 Drawing Sheet

OTHER PUBLICATIONS

Ford APDW, Arredondo NF, Blue DR, Bonhaus DW, Jasper J Kava MS, Lesnick J, Pfister JR, Shieh IA, Vimont RL., Williams TJ, McNeal JE, Stamey TA, and Clarke DE (1996) RS–17053 (N–[2–(2–Cyclopropylmethoxyphenoxy)ethyl] –5–chloro–a, a–dimethyl–1H–indole–3–ethanamine hydrochloride), a selective $\alpha$1A–adrenoceptor antagonist, displays low affinity for functional $\alpha$1–adrenoceptors in human prostate: Implications for adrenoceptor classification. Mol. Pharmacol. 49: 209–215.

Forray C, Bard JA, Wegzel JM, Chiu G, Shapiro E, Tang R, Lepor H, Hartig PR, Weinshank RL, Branchek TA, and Gluchowski C (1994) The $\alpha$1–adrenergic receptor that mediates smooth muscle contraction in human prostate has the pharmacological properties of the cloned human $\alpha$1c subtype. Mol. Pharmacol. 45: 703–708.

Gormley G, Stoner E, Bruskewitz RC et al. (1992) The effect of finasteride in men with benign prostatic hyperplasia. N. Engl. J. Med. 327: 1185–1191.

Hatano A, Takahashi H, Tamaki M, Komeyama T, Koizumi T, and Takeda M (1994) Pharmacological evidence of distinct $\alpha$1–adrenoceptor subtypes mediating the contraction of human prostatic urethra and peripheral artery. Br. J. Pharmacol. 113: 723–728.

Harrison JK, Pearson WR, and Lynch KR (1991) Molecular characterization of $\alpha$1–and $\alpha$2–adrenoceptors. Trends Pharmacol. Sci. 12: 62–67.

Hieble JP and Caine M (1986) Etiology of benign prostatic hyperlasia and approaches to pharmacological management. Fed. Proc. 45: 2601–2603.

Hirasawa A, Horie K, Tanaka T, Takagaki K, Murai M, Yano J. and Tsujimoto G (1993) Cloning, functional expression and tissue distribution of human cDNA for the $\alpha$1c–adrenergic receptor. Biochem. Biophys. Res. Commun. 195: 902–909.

Holck MI, Jones CHM, and Haeusler G (1983) Differential interactions of clonidine and methoxamine with postsynaptic $\alpha$–adrenoceptors of rabbit main pulmonary artery. J.Cardiovasc. Pharm. 5: 240–248.

Lepor H, Auerbach S, Puras–Baez A et al. (1992) A randomized, placebo–controlled multicenter study of the efficacy and safety of terazosin in the treatment of benign prostatic hyperplasia. J. Urol. 148: 1467–1474.

Lepor H (1995) $\alpha$–Blockade for benign prostatic hyperplasia (BPH) J. Clin. Endocrinol. Metab. 80: 750–753.

Marshall I, Burt RP, Andersson PO, Chapple CR, Greengrass PM, Johnson GI, and Wyllie MG (1992) Human $\alpha$1c–adrenoceptor: functional characterisation in prostate. Br. J. Pharmacol. 107(Proc. Suppl. Dec.):327P.

Marshall I, Burt RP, and Chapple CR (1995) Noradrenaline contractions of human prostate mediated by $\alpha$1A–($\alpha$1c–) adrenoceptor subtype. Br. J. Pharmacol. 115: 781–786.

Mebust WK, Holtgrewe HL, Cockett ATK, and Peters PC (1989) Transurethral prostatectomy: immediate and postoperative complication: a cooperative study of 13 participating institutions evaluating 3,885 patients.J. Urol., 141 :243–247.

Minneman KP, Han C and Abel PW (1988) Comparison of $\alpha$1–adrenergic receptor subtypes distinguished by chloroethylclonidine and WB4101. Mol. Pharmacol. 33: 509–514.

Minneman KP and Esbenshade TA (1994) $\alpha$1–Adrenergic receptor subtypes. Annu. Rev. Pharmacol. Toxicol. 34: 117–133.

Morrow AL and Creese I (1986) Characterization of $\alpha$1–adrenergic receptor subtypes in rat brain: A reevaluation of [3H]WB4104 and [3H]prazosin binding. Mol. Pharmacol. 29: 321–330.

Muramatsu I, Oshita M, Ohmura T, Kigoshi S, Akino H, Gobara M, and Okada K (1994) Pharmacological characterization of $\alpha$1–adrenoceptor subtypes in the human prostate: functional and binding studies. Br. J. Urol. 74: 572–577.

Oesterling JE (1995) Benign prostatic hyperplasia. Medical and minimally invasive treatment options. N. Engl. J. Med. 332: 99–109.

Price DT, Lefkowitz RJ, Caron MG, Berkowitz D, and Schwinn DA (1994) Localization of mRNA for three distinct $\alpha$1–adrenergic receptor subtypes in human tissues: implications for human $\alpha$–adrenergic physiology. Mol. Pharmacol. 45: 171–175.

Ramarao CS, Kincade Denker JM, Perez DM, Gaivin RJ, Riek RP, and Graham RM (1992) Genomic organization and expression of the human $\alpha$1B–adrenergic receptor. J. Biol. Chem. 267: 21936–21945.

Schwinn DA, Johnston GI, Page SO, Mosley MJ, Wilson KH, Worman NP, Campbell S, Fidock MD, Furness LM, Parry–Smith DJ, Peter B, and Bailey DS (1995) Cloning and pharmacological characterization of human alpha–1 adrenergic receptors: sequence corrections and direct comparison with other species homologues. JPET 272: 134–142.

Weinberg DH, Trivedi P, Tan CP, Mitra S, Perkins–Barrow A, Borkowski D, Strader CD, and Bayne M (1994) Cloning, expression and characterization of human $\alpha$ adrenergic receptors $\alpha$1A, $\alpha$1B, and $\alpha$1C. Biochem. Biophys. Res. Commun. 201: 1296–1304.

Weis KA, Epstein RS, Huse DM, Deverka PA and Oster G (1993) The costs of prostatectomy for benign prostatic hyperplasia. Prostate 22: 325–334.

Wennberg JE, Roos N, Sola L, Schori A, and Jaffe R (1987) Use of claims data systems to evaluate health care outcomes: mortality and reoperation following prostatectomy. JAMA 257: 933–936.

Yamada S, Tanaka C, Kimura R, and Kawabe K (1994) Alpha 1–adrenoceptors in human prostate: characterization and binding characteristics of alpha 1–antagonists. Life Sci. 54: 1845–1854.

Effects of Compound 3 upon IUP and MAP at 10 μg/kg PE in dogs

HETEROCYCLES USEFUL IN THE TREATMENT OF BENIGN PROSTATIC HYPERPLASIA

This application claims benefit of U.S. provisional application 60/061,618 filed Oct. 9, 1997.

This invention relates to a series of aryl piperazine substituted heterocycles, pharmaceutical compositions containing them and intermediates used in their manufacture. The compounds of the invention selectively inhibit binding to the α-1a adrenergic receptor, a receptor which has been implicated in benign prostatic hyperplasia. As such the compounds are potentially useful in the treatment of this disease.

BACKGROUND

Benign prostatic hyperplasia (BPH), a nonmalignant enlargement of the prostate, is the most common benign tumor in men. Approximately 50% of all men older than 65 years have some degree of BPH and a third of these men have clinical symptoms consistent with bladder outlet obstruction (Hieble and Caine, 1986). In the U.S., benign and malignant diseases of the prostate are responsible for more surgery than diseases of any other organ in men over the age of fifty.

There are two components of BPH, a static and a dynamic component. The static component is due to enlargement of the prostate gland, which may result in compression of the urethra and obstruction to the flow of urine from the bladder. The dynamic component is due to increased smooth muscle tone of the bladder neck and the prostate itself (which interferes with emptying of the bladder) and is regulated by alpha 1 adrenergic receptors (α1-ARs). The medical treatments available for BPH address these components to varying degrees, and the therapeutic choices are expanding.

Surgical treatment options address the static component of BPH and include transurethral resection of the prostate (TURP), transurethral incision of the prostate (TUIP), open prostatectomy, balloon dilatation, hyperthermia, stents and laser ablation. TURP is the gold standard treatment for patients with BPH and approximately 320,000 TURPs were performed in the U.S. in 1990 at an estimated cost of $2.2 billion (Weis et al., 1993). Although an effective treatment for most men with symptomatic BPH, approximately 20–25% of patients do not have a satisfactory long-term outcome (Lepor and Rigaud, 1990). Complications include retrograde ejaculation (70–75% of patients), impotence (5–10%), postoperative urinary tract infection (5–10%), and some degree of urinary incontinence (2–4%) (Mebust et al., 1989). Furthermore, the rate of reoperation is approximately 15–20% in men evaluated for 10 years or longer (Wennberg et al., 1987).

Apart from surgical approaches, there are some drug therapies which address the static component of this condition. Finasteride (Proscar . . . , Merck), is one such therapy which is indicated for the treatment of symptomatic BPH. This drug is a competitive inhibitor of the enzyme 5a-reductase which is responsible for the conversion of testosterone to dihydrotestosterone in the prostate gland (Gormley et al., 1992). Dihydrotestosterone appears to be the major mitogen for prostate growth, and agents which inhibit 5a-reductase reduce the size of the prostate and improve urine flow through the prostatic urethra. Although finasteride is a potent 5a-reductase inhibitor and causes a marked decrease in serum and tissue concentrations of dihydrotestosterone, it is only moderately effective in treating symptomatic BPH (Oesterling, 1995). The effects of finasteride take 6–12 months to become evident and for many men the clinical improvement is minimal (Barry, 1997).

The dynamic component of BPH has been addressed by the use of adrenergic receptor blocking agents (a1-AR blockers) which act by decreasing the smooth muscle tone within the prostate gland itself. A variety of a1-AR blockers (terazosin, prazosin, and doxazosin) have been investigated for the treatment of symptomatic bladder outlet obstruction due to BPH, with terazosin (Hytrin . . . , Abbott) being the most extensively studied. Although the α1-AR blockers are well-tolerated, approximately 10–15% of patients develop a clinically adverse event (Lepor, 1995). The undesirable effects of all members of this class are similar, with postural hypotension being the most commonly experienced side effect (Lepor et al., 1992). In comparison to the 5a-reductase inhibitors, the α1-AR blocking agents have a more rapid onset of action (Steers, 1995). However, their therapeutic effect, as measured by improvement in the symptom score and the peak urinary flow rate, is moderate. (Oesterling, 1995) The use of α1-AR antagonists in the treatment of BPH is related to their ability to decrease the tone of prostatic smooth muscle, leading to relief of the obstructive symptoms. Adrenergic receptors are found throughout the body play a dominant role in the control of blood pressure, nasal congestion, prostrate function and other processes (Harrison et al., 1991). However, there are a number of cloned a 1-AR receptor subtypes: α1a-AR, α1b-AR and α1d-AR (Bruno et al., 1991; Forray et al., 1994; Hirasawa et al., 1993; Ramarao et al., 1992; Schwinn et al., 1995; Weinberg et al., 1994). A number of labs have characterized the α1-ARs in human prostate by functional, radioligand binding, and molecular biological techniques (Forray et al., 1994; Hatano et al., 1994; Marshall et al., 1992; Marshall et al., 1995; Yamada et al., 1994). These studies provide evidence in support of the concept that the α1-AR subtype comprises the majority of α1-ARs in human prostatic smooth muscle and mediates contraction in this tissue. These findings suggest that the development of a subtype-selective α1a-AR antagonist might result in a therapeutically effective agent with reduced side effects for the treatment of BPH.

The compounds of this invention selectively bind to the α1a-AR receptor, antagonize the activity of said receptor and are selective for prostate tissue over aortic tissue. As such, these represent a viable treatment for BHP without the side effects associated with known α1-AR antagonists.

SUMMARY OF THE INVENTION

The invention relates to compounds of Formula I

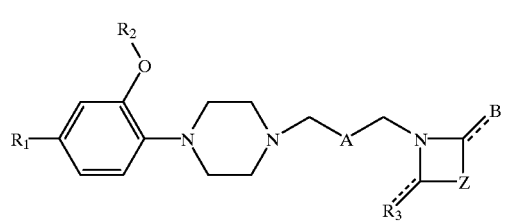

wherein:
 $R_1$ is hydrogen, halogen, $C_{1-5}$alkoxy, hydroxyl, or $C_{1-6}$alkyl;
 $R_2$ is $C_{1-6}$alkyl, substituted $C_{1-6}$alkyl
   where the alkyl substituents are one or more halogens, phenyl, substituted phenyl where the phenyl substituents are independently selected from one or more of the group consisting of $C_{1-5}$alkyl, $C_{1-5}$alkoxy, and trihalo$C_{1-5}$alkyl), phenyl$C_{1-5}$alkyl, or substituted phenyl$C_{1-5}$alkyl where the phenyl substituents are independently selected from one or more of the group consisting of $C_{1-5}$alkyl, halogen, $C_{1-5}$alkoxy, and trihalo$C_{1-5}$alkyl;

$R_3$ is hydrogen, $C_{1-5}$alkoxycarbonyl, $C_{1-5}$alkyl, hydroxy$C_{1-5}$alkyl, formyl, acetyl, amido, or oxygen where if $R_3$ is oxygen the hashed line is solid is taken together with the other solid line to represent a double bond, and if $R_3$ is not oxygen, the hashed line represents a single bond affixed to a hydrogen;

A is selected from the group consisting of

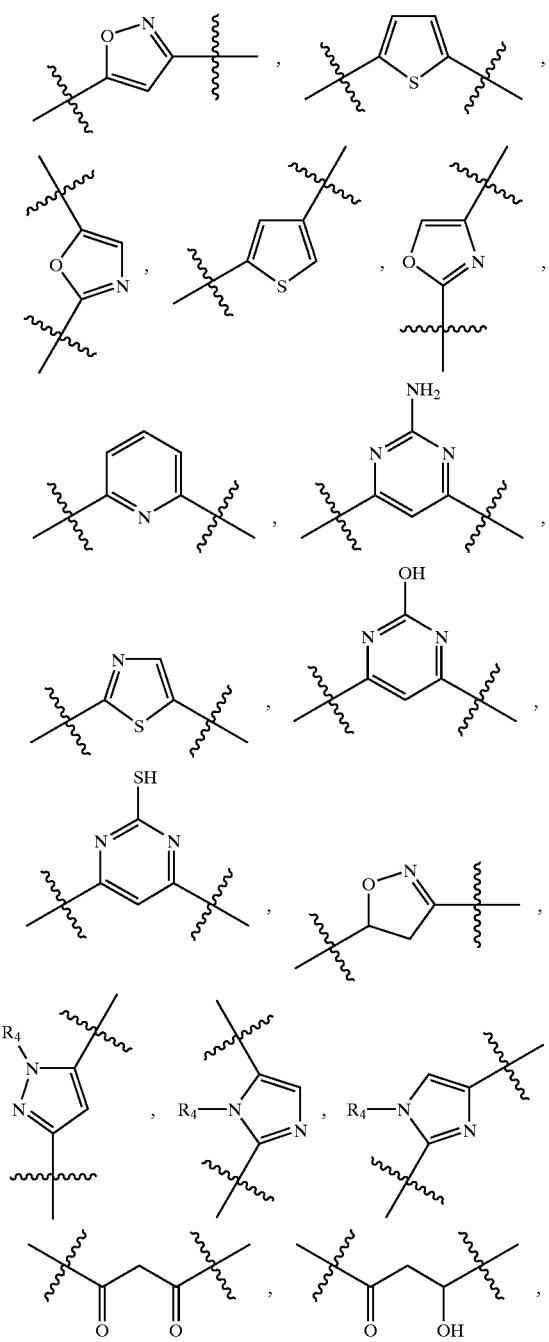

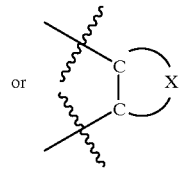

where the points of attachment are depicted by the hashed bonds,
where one point of attachment is bonded to the methylene adjacent to the depicted piperazine and the second point of attachment is bonded to the other methylene;

$R_4$ is hydrogen or $C_{1-5}$alkyl;

B is hydrogen or oxygen,
where if B is oxygen the hashed line is solid and is taken together with the other solid line to represent a double bond, and if B is hydrogen the hashed line represents a single bond affixed to a hydrogen;

Z is —(CH$_2$)$_n$— where n is 1–5, —CH$_2$—CR$_5$R$_6$—CH$_2$—, —CHR$_5$R$_6$CH—
where $R_5$ and $R_6$ are hydrogen, $C_{1-5}$alkyl or taken together to form a $C_{3-8}$cycloalkane,

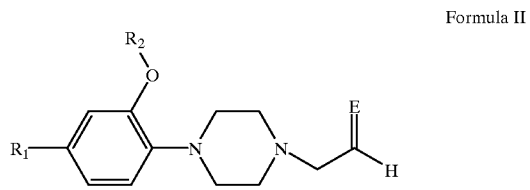

where ring X is an aromatic ring of 6 members;
or pharmaceutically acceptable salts thereof.

Aside form the compounds of Formula I, the invention contemplates compounds of Formula II and Formula III. These compounds are useful as intermediates in the preparation of compounds of Formula I and are as follows:

Formula II wherein:
$R_1$ is hydrogen, halogen, $C_{1-5}$alkoxy, hydroxyl, or $C_{1-6}$alkyl;
$R_2$ is $C_{1-6}$alkyl, substituted $C_{1-6}$alkyl
where the alkyl substituents are one or more halogens, phenyl, substituted phenyl
where the phenyl substituents are independently selected from one or more of the group consisting of $C_{1-5}$alkyl, $C_{1-5}$alkoxy, and trihalo$C_{1-5}$alkyl), phenyl$C_{1-5}$alkyl, or substituted phenyl$C_{1-5}$alkyl
where the phenyl substituents are independently selected from one or more of the group consisting of $C_{1-5}$alkyl, halogen, $C_{1-5}$alkoxy, and trihalo$C_{1-5}$alkyl; and D is oxygen or N—OH.

Formula III

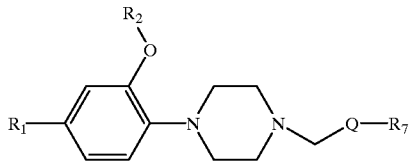

wherein:
  $R_1$ is hydrogen, halogen, $C_{1-5}$alkoxy, hydroxyl, or $C_{1-6}$alkyl;
  $R_2$ is $C_{1-6}$alkyl, substituted $C_{1-6}$alkyl
    where the alkyl substituents are one or more halogens, phenyl, substituted phenyl
    where the phenyl substituents are independently selected from one or more of the group consisting of $C_{1-5}$alkyl, $C_{1-5}$alkoxy, and trihalo$C_{1-5}$alkyl), phenyl$C_{1-5}$alkyl, or substituted phenyl$C_{1-5}$alkyl
    where the phenyl substituents are independently selected from one or more of the group consisting of $C_{1-5}$alkyl, halogen, $C_{1-5}$alkoxy, and trihalo$C_{1-5}$alkyl; and
  Q is selected from the group consisting of

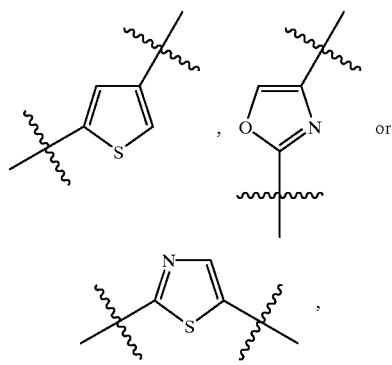

where the points of attachment are depicted by the hashed bonds,
  where one point of attachment is bonded to the methylene adjacent to the depicted piperazine and the second point of attachment is bonded to $R_9$;
  where $R_7$ is formyl, halomethyl, hydroxymethyl, t-butyldiphenylsilyloxymethyl, $C_{1-6}$alkoxycarbonyl, and carboxy.

DETAILED DESCRIPTION OF THE INVENTION

Figure 1:
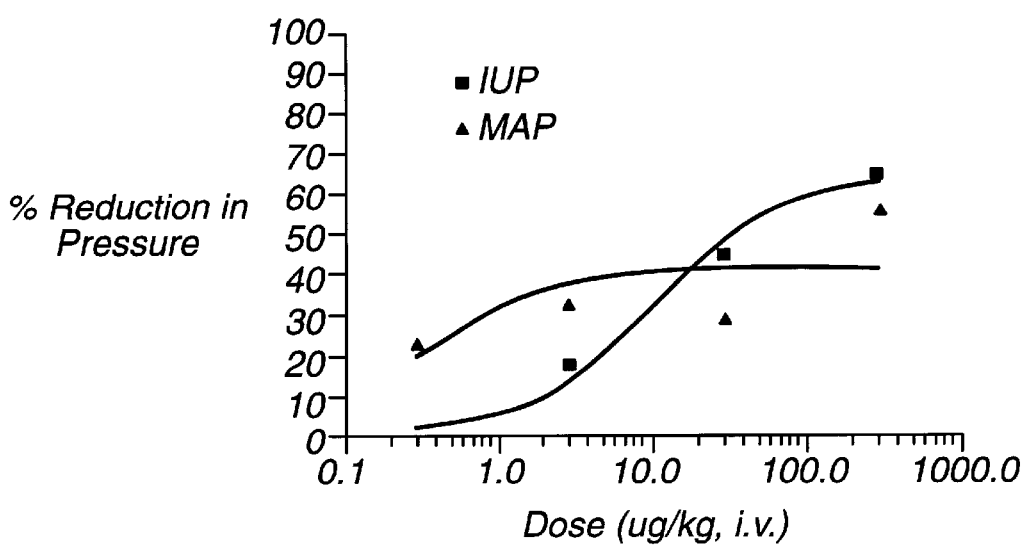
FIG. 1 illustrates the mean percentage reductions in the intraurethral pressure (IUP) and the mean arterial pressure (MAP) for a representative compound of the invention.

The terms used in describing the invention are commonly used and known to those skilled in the art. However, the terms that could have other meanings are defined. "HBSS" refers to Hank's Balanced Salt Solution. "Independently" means that when there are more than one substituent, the substitutents may be different. The term "alkyl" refers to straight, cyclic and branched-chain alkyl groups and "alkoxy" refers to O-alkyl where alkyl is as defined supra.

"LDA" refers to lithium diiopropylamide, and "LAH" refers to lithium aluminum hydride. The symbol "Ph" refers to phenyl, and "aryl" includes mono and fused aromatic rings such as phenyl and naphthyl. The symbol "CPDA" refers to 1,1-cyclopentanediacetimid-1-yl and "IID" refers to 1H-isoindole 1,3(2H)dion-1-yl.

The compounds of the invention may be prepared by the following schemes, where some schemes produce more than one embodiment of the invention. In those cases, the choice of scheme is a matter of discretion which is within the capabilities of those skilled in the art.

The compounds of Formula I where $R_1$ is hydrogen, $R_2$ is phenyl, $R_3$ is hydrogen, A is 2-mercaptopyrimidine, B is oxygen and Z is $(CH_2)_4$ may be prepared using Scheme 1. The starting material for this scheme is a mono N-substituted piperazine of type 1a. This starting material is treated at reflux for about 18–24 h with a mild base such as $K_2CO_3$ and an alkylating agent such as chloroacetone to give intermediate 1b. Compound 1b may be treated with a strong base, such as NaH and reagent 1c, such as hexahydro-2-oxo-1H-azepine-1-acetic acid ethyl ester, at 0° C. to room temperature over 1–16 h, to give the diketo compound 1d. This compound may be treated with may be treated with a mild base such as sodium acetate, reagent 1e, such as thiourea, in an alcoholic solvent such as EtOH at about room temperature to reflux over 1–3 days to give a compound of Formula 1 where $R_2$ is phenyl, A is 2-mercaptopyrimidine, and Z is $(CH_2)_4$.

Aside from the illustrated compound, Scheme 1 may be used to prepare a number of other compounds of the invention. For example, to prepare compounds where A is 2-hydroxypyrimidine, reagent 1e is replaced with urea and the remaining steps of the scheme are executed as described. To prepare compounds where A is pyrazole, the illustrated reagent 1e, is replaced with hydrazine and the remaining steps are carried out as described. To prepare compounds where A is pyrazole and $R_4$ is $C_{1-5}$alkyl, reagent 1e is replaced with an appropriately substituted N-alkylhydrazine. Compounds where A is isoxazole may be prepared using this scheme. Treatment of intermediate 1d with hydroxylamine hydrochloride and an equivalent of an organic base, such as pyridine in an alcoholic solvent such as methanol over several hours at 20–100° C. gives the desired products. Aside from the heterocyclic A substituents, Scheme I may be used to prepare compounds of Formula 1 where A is

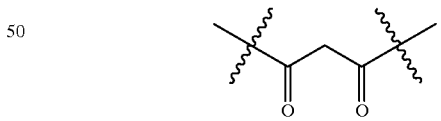

In addition to modifications of A, Scheme 1 may be used to prepare compounds where Z is $(CH_2)_{1-5}$. The substitution of the illustrated reagent 1c with another known cyclic lactam gives the desired compounds. For example to prepare compounds where Z is $CH_2$, replace hexahydro-7-oxo-1H-azepine-2-carboxylic acid, with 4-oxo-2-azetidine carboxylic acid ethyl ester. In order to modify $R_1$ and $R_2$ known phenyl substituted piperazines may be used in place of 1a. For example to prepare a compound where $R_1$ is fluoro and $R_2$ is 2,2,2-trifluoroethyl, 1-(2-phenoxy)phenylpiperazine is replaced with 1-[4-fluoro-2-(2,2,2-trifluoroethoxy)phenyl] piperazine.

Scheme 1

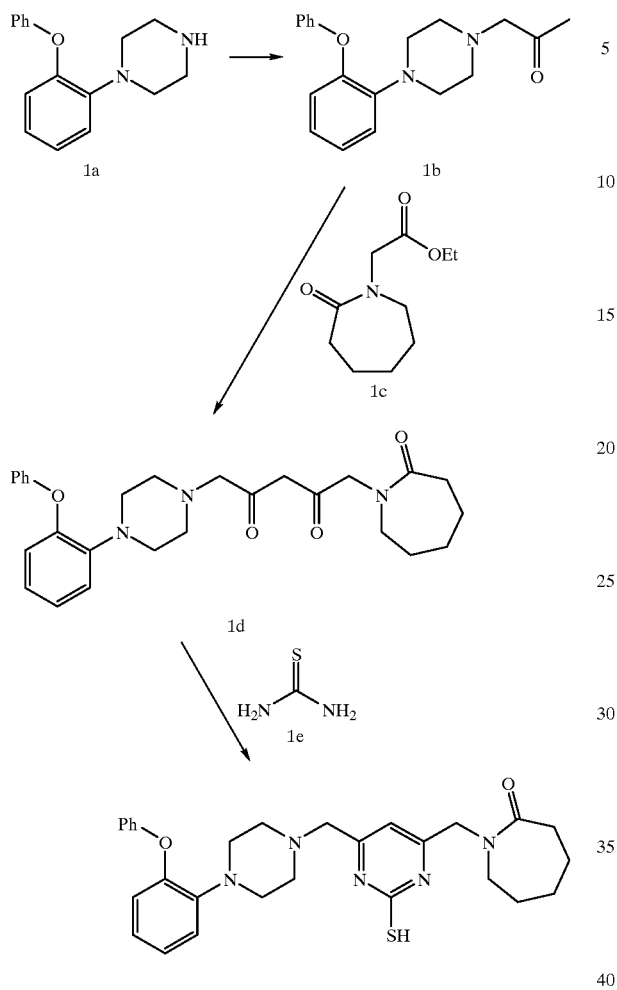

Scheme 2

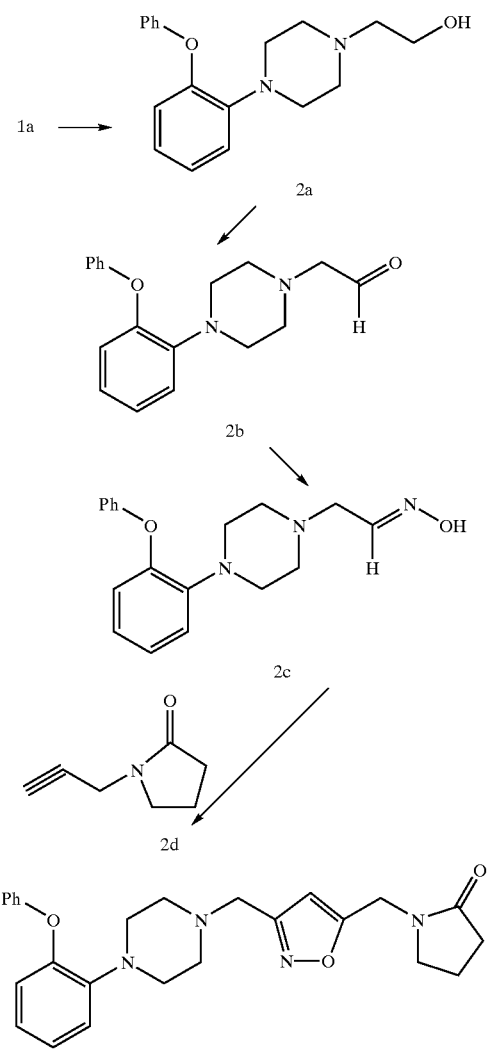

Scheme 2 may be used to prepare compounds of the invention where $R_1$ is hydrogen, $R_2$ is phenyl, $R_3$ is hydrogen, A is isoxazole, B is oxygen and Z is $(CH_2)_2$. Reagent 1a may be treated with bromoethanol and a mild base such as $K_2CO_3$ in an inert solvent such as THF at reflux over several days to give the alcohol 2a. Treatment of 2a with DMSO and oxalyl chloride and triethylamine in THF for several hours at a temperature range of −78° C. to room temperature give the aldehyde 2b. Subsequent treatment of 2b with hydroxylamine in an alcoholic solvent such as ethanol at room temperature over 8–36 hours gives the oxime 2c. Treatment of 2c with the lactam 2d, aqueous NaOCl and a trace of triethylamine at room temperature over several days gives a compound of Formula I where $R_1$ is hydrogen, $R_2$ is phenyl, $R_3$ is hydrogen, A is isoxazole, B is oxygen and Z is $(CH_2)_2$. Aside from the illustrated product, Scheme 2 may be used to prepare a variety of compounds of the invention. For example to prepare a compound where A is 3,4-dihydroisoxazole and Z is $(CH_2)_4$, reagent 2d is replaced with hexahydro-1-(2-propenyl)-2H-azepine-2-one. To prepare compounds where Z is $(CH_2)_3$ and A is isoxazole replace 2d with hexahydro-1-(2-propynyl)-2H-azepine-2-one. To prepared compounds where $R_1$ and $R_2$ are other than phenyl and hydrogen, respectively, the starting piperazine may be modified as suggested in Scheme 1.

As illustrated, Scheme 3 may be used to produce compounds of the invention where $R_1$ is chlorine, $R_2$ is methyl, $R_3$ is hydrogen, A is oxazole, B is oxygen and Z is $(CH_2)_2$. Treatment of 3a, 2-bromomethyl-4-carbomethoxyoxazole, with an analogue of starting material 1a, namely 1-[4-chloro-2-methoxyphenyl]piperazine, and an organic base such as diisopropylethylamine in an inert solvent at reflux for 1–16 h gives the coupled intermediate 3b. Successive treatment of 3b with a reducing agent such as $NaBH_4$ at room temperature to reflux, followed by a halogenating agent such as thionyl chloride at room temperature gives the chloride 3c. Treatment of the chloride 3c with a cyclic lactam 3d, such as 2-pyrrolidinone, and a strong base such as potassium hydride, in an inert solvent such as THF over several minutes to 6 h at room temperature gives the illustrated compound of Formula 1.

This scheme may be used to prepare compounds of the invention where A is thiazole. One can replace 3a with 2-bromomethyl-4-carboethoxythiazole and carry out the remaining steps of Scheme 3 to obtain those compounds. To prepare compounds where $R_3$ is alkyl, replace 3d with an alkylated lactam such as 6-methyl-2-piperidone. If compounds where $R_3$ is $C_{1-5}$alkoxycarbonyl are desired, replace 3d with 6-oxo-2-piperidine carboxylic acid ethyl ester. In addition one can prepare compounds where B is hydrogen by replacing 3d with cyclic amines such as piperidine. As in other schemes, modifications of the substitution patterns at $R_1$, $R_2$ and Z may be accomplished by using analogues of 1a and 3d respectively. In addition to the aforementioned products, Scheme 3 may be used to produce compounds where A is imidazole. For example to produce compounds where A is thiazole replace the illustrated starting material 3a with ethyl-2-(bromomethyl)imidazole-4-carboxylate and follow the remaining steps of Scheme 3.

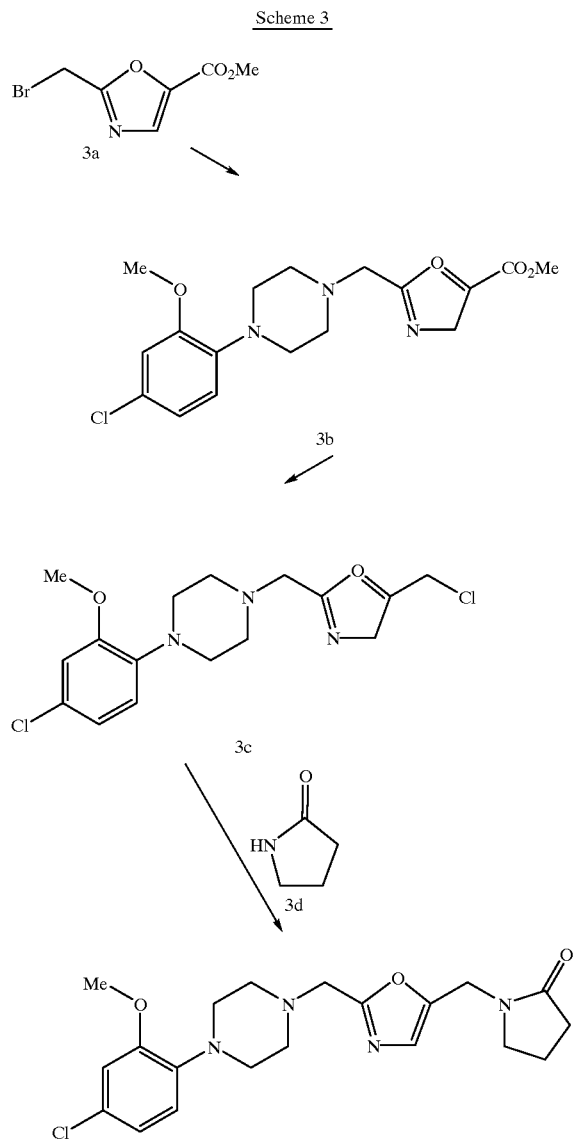

Scheme 4 may be used to prepare compounds where $R_1$ is chlorine, $R_2$ is methyl, $R_3$ is hydrogen A is pyridine, B is oxygen and Z is $(CH_2)_4$. Reactant 4a, 2,6-bischloromethylpyridine, is treated with a 1a analogue and an organic base such as pyridine at reflux for about 1–5 h to give the coupled product 4b. Treatment of 4b with a cyclic lactam derivative, 4c, a strong base such a n-BuLi in an inert solvent from 0° C. to reflux give the illustrated compound of Formula I. In addition to the illustrated compounds Scheme 4 may be used to synthesize compounds where $R_1$, $R_2$, $R_3$, B, and Z are other than chlorine, methoxy, hydrogen, oxygen, and $(CH_2)_4$ respectively as stated in Schemes 1–3.

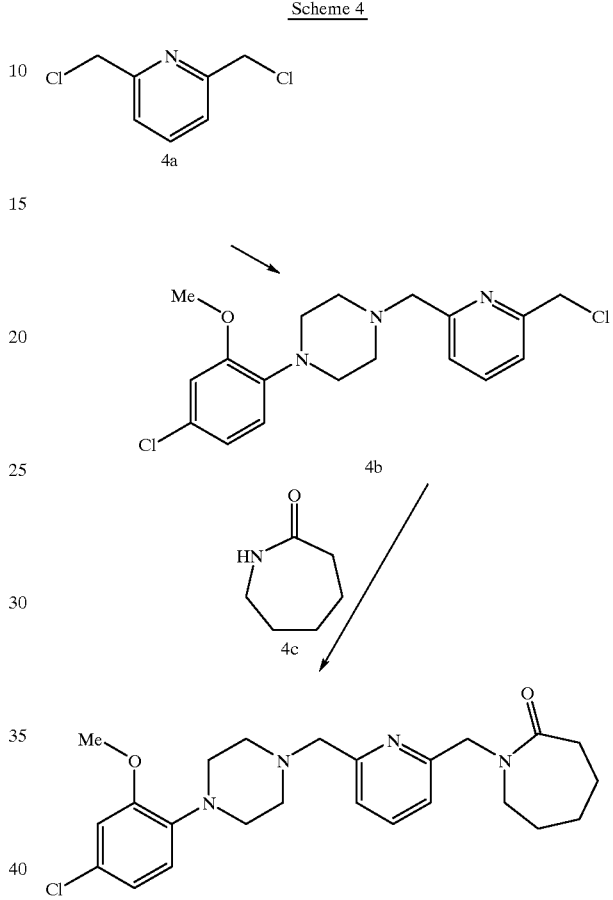

To prepare compounds where A is thiophene, Scheme 5 may be used. Reagent 5a, 2-bromo-5-thiophenecarboxaldehyde, may be treated with an analogue of 1a, $NaBH(OAc)_3$ and acetic acid in an inert solvent such as methylene chloride at room temperature for about 3–10 h to give the coupled product 5b. Treatment of 5b with a strong base such as n-butyllithium and DMF at −78° C. to 0° C. gives the aldehyde 5c. This intermediate may be treated with a reducing agent such as $NaBH_4$ to give the alcohol 5d. This alcohol is treated with thionyl chloride in an inert solvent such as methylene chloride at room temperature for about 6 h; and is subsequently treated with a cyclic lactam and a strong base such a NaH in an inert solvent such as DMF at room temperature to give a compound of Formula I. Although the illustrated product of Scheme 5 is a 2,5-substituted thiophene, the scheme may be used to produce 2,4-substitutied thiophenes. The 2,4-substituted compounds may be produced by substituting 2-bromo-4-thiophenecarboxaldehyde, for the illustrated reagent 5a. In addition this scheme may be used to prepare all of the $R_1$, $R_2$, $R_3$, B and Z substitutions of the invention as discussed in previous schemes.

Scheme 5

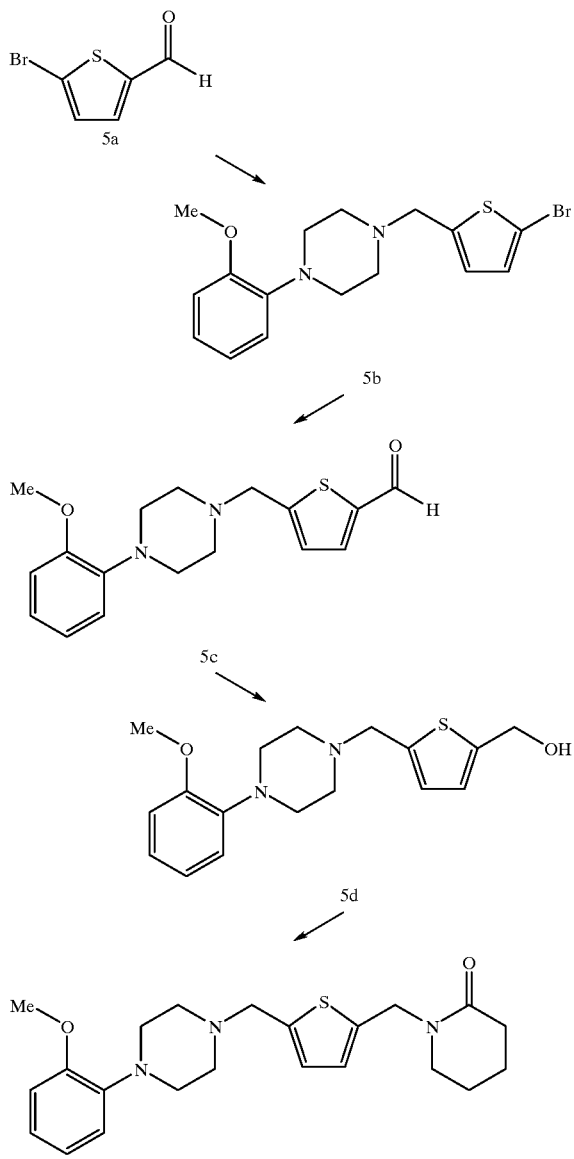

Scheme 6

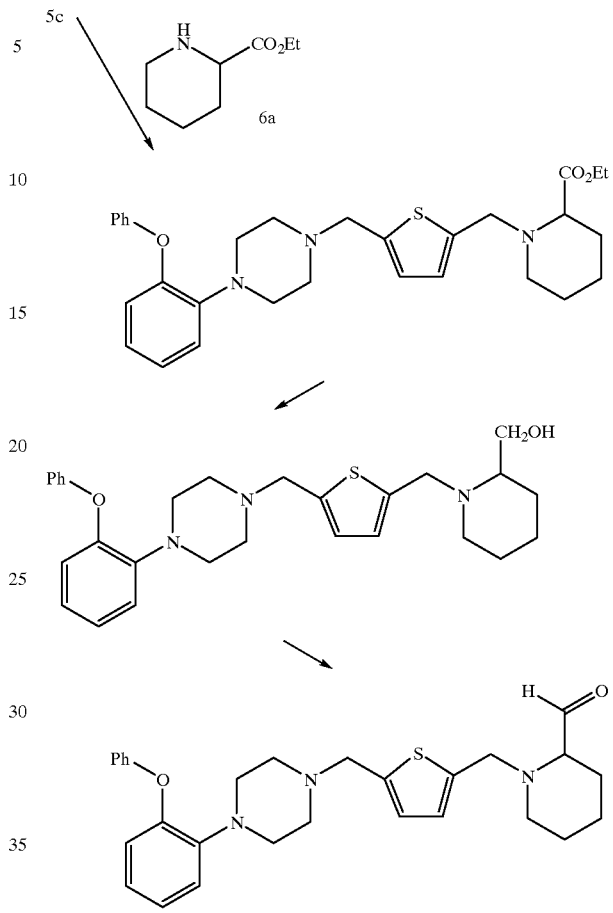

The products of Scheme 5 may be used to prepare other compounds as illustrated by Scheme 6. To produce compounds of the invention where B is hydrogen, A is thiophene, $R_2$ is phenyl, $R_3$ is carboethoxy, and Z is $(CH_2)_3$ the 2-phenoxy analog of intermediate 5c may be treated with NaBH(OAc)3, triethyl amine and reactant 6a, 2-piperidinecarboxylic acid ethyl ester hydrochloride, at room temperature over 4–12 h to give the desired ester derivative of Formula I Aside from the illustrated ester derivative, Scheme 5 may be used to prepare the hydroxymethyl derivative by treating the ester with $NaBH_4$ and an inert solvent, such as methanol, at room temperature over 30 min. This hydroxymethyl derivative could be oxidized under standard Swern conditions to give the corresponding aldehyde.

To prepare compounds where B is oxygen, A is isoxazole, $R_2$ is phenyl, $R_3$ is carboethoxy and Z is $(CH_2)_3$ Scheme 7 may be used. Treatment of 1a with propargyl bromide and a mild base such as $K_2CO_3$, in an inert solvent such as acetonitrile gives the alkynyl intermediate 7a. Treatment of 7a with triethylamine, 2-(2-nitroethoxy)tetrahydropyran and phenyl isocyanate in an inert solvent such as toluene at about 60° C. over 24 to 48 h followed by treatment with aqueous acid at room temperature over 1–5 h gives the alcohol intermediate 7b. Intermediate 7b may be treated with thionyl chloride in an inert solvent such as methylene chloride at room temperature over 1–12 h to give the chloride 7c. Treatment of 7c with one equivalent of a strong base, such as NaH and reactant 7d, namely 6-oxo-2-piperidine carboxylic acid ethyl ester in an inert solvent such as DMF at room temperature over 10–24 h gives the desired compound of Formula I.

In addition to the illustrated product, Scheme 7 may be used to produce compounds of the invention where B is hydrogen. Replacement of reagent 7d with another cyclic lactam such as proline methyl ester gives a compound of the invention where B is hydrogen, A is isoxazole, $R_2$ is phenyl, $R_3$ is carboethoxy and Z is $(CH_2)_1$. Aside from the aforementioned products, Scheme 7 may be used to prepare all of the $R_1$, $R_2$ $R_3$, B, and Z substitutions of the invention as discussed in previous schemes.

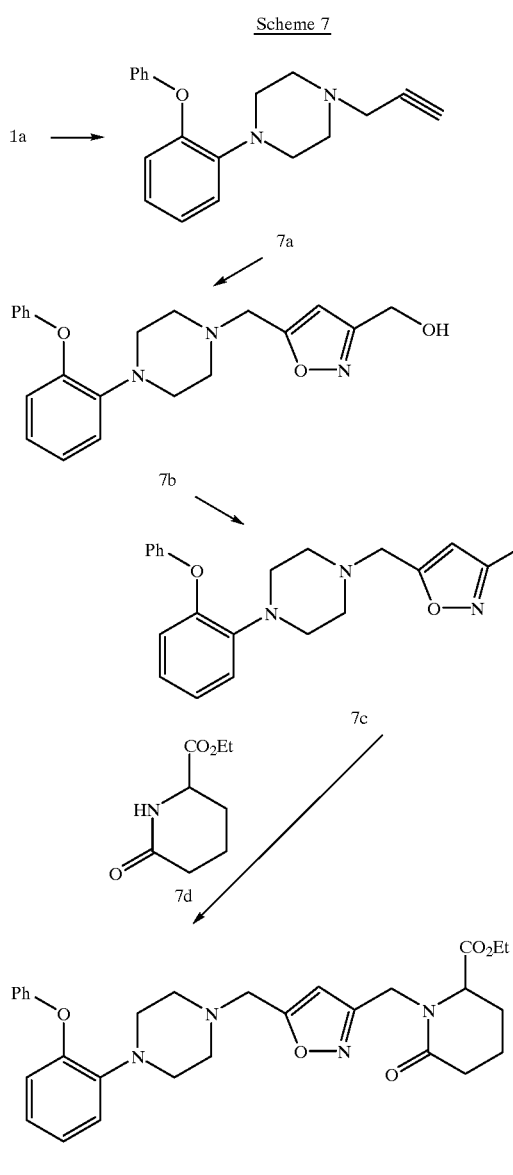

Scheme 7

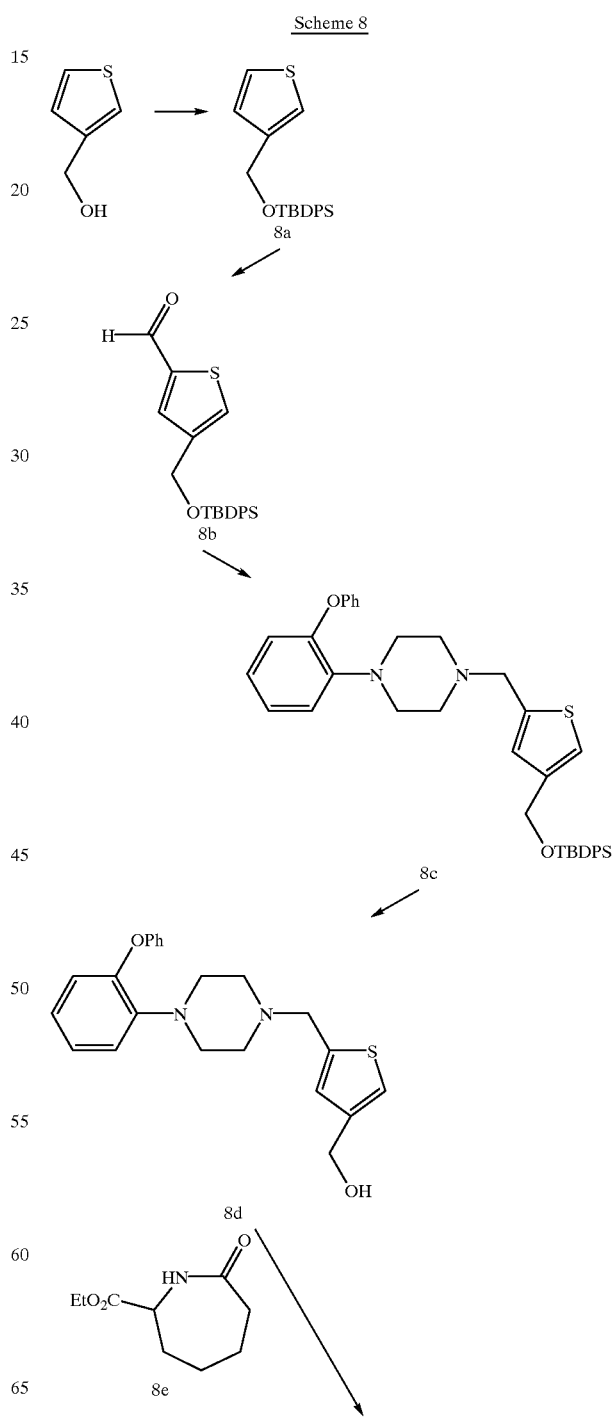

Scheme 8 hydrogen. Replacement of reagent 8e with another cyclic lactam such as proline methyl ester gives a compound of the invention where B is hydrogen, A is thiophene, $R_2$ is phenyl, $R_3$ is carboethoxy and Z is $(CH_2)_2$. Compounds where B is hydrogen and $R_3$ is hydrogen may also be prepared in this manner by this scheme. Replacement of 8d with proline gives a compound of the invention where B is hydrogen, A is thiophene, $R_2$ is phenyl, $R_3$ is hydrogen and Z is $(CH_2)_2$. Aside from the aforementioned products, Scheme 8 may be used to prepare all of the $R_1$, $R_2$ $R_3$, B and Z substitutions of the invention as discussed in previous schemes.

To prepare compounds of the invention where B is oxygen, A is thiophene, $R_2$ is phenyl, $R_3$ is carboethoxy and Z is $(CH_2)_4$ Scheme 8 may be used. Treatment of 3-thiophenemethanol with a silylating agent such as t-butyldiphenylchlorosilane and imidazole at room temperature in an inert solvent such as DMF over 10–48 h gives intermediate 8a. This intermediate may be formylated with DMF and a strong base such as t-butyllithium at about −78° C. over 30 min to 2 h to give the aldehyde 8b. Reductive amination of the aldehyde with intermediate 1a, NaBH(OAc)$_3$ and glacial acetic acid at room temperature over 3–6 h gives the coupled intermediate 8c. This intermediate may be deprotected with tetrabutylammonium fluoride in THF at room temperature to give alcohol 8d. This alcohol may be chlorinated with thionyl chloride and an inert solvent such as methylene chloride at room temperature for 1–10 h and subsequently coupled with reagent 8e. A strong base such as NaH and a suitable solvent such as DMF facilitate this reaction which proceeds at room temperature over 10–24 h to give the desired compound of Formula 1.

In addition to the illustrated product, Scheme 8 may be used to produce compounds of the invention where B is -continued

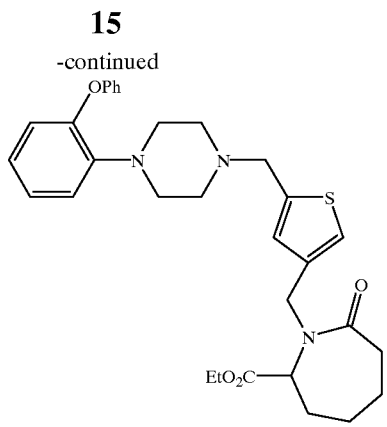

To prepare compounds where A is

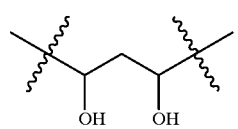

Scheme 9 may be used. Treatment of compound 1d with a reducing gent such as NaBH$_4$ in a suitable solvent such as MeOH tive the desired diol. Aside from the diol, this scheme may be used to prepare compounds where A is

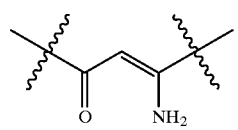

Compound 1d may be treated with aqueous ammonium hydroxide at room temperature over several days to give the unsaturated product as a mixture of regioisomers. This product may be treated with a reducing agent such as sodium in liquid ammonia at about −33° C. over 2–8 h to give the desired saturated product.

Scheme 9

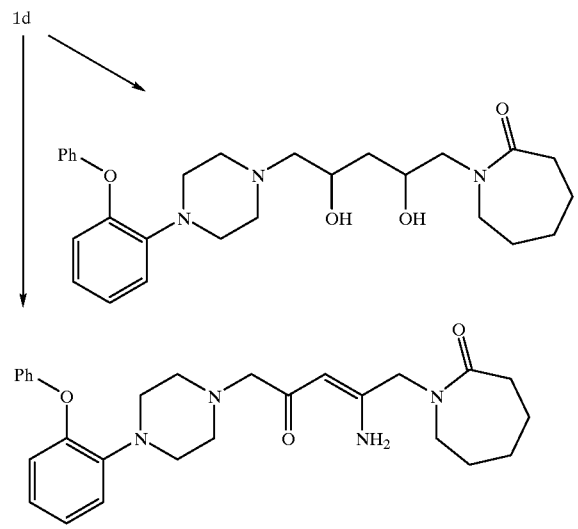

-continued

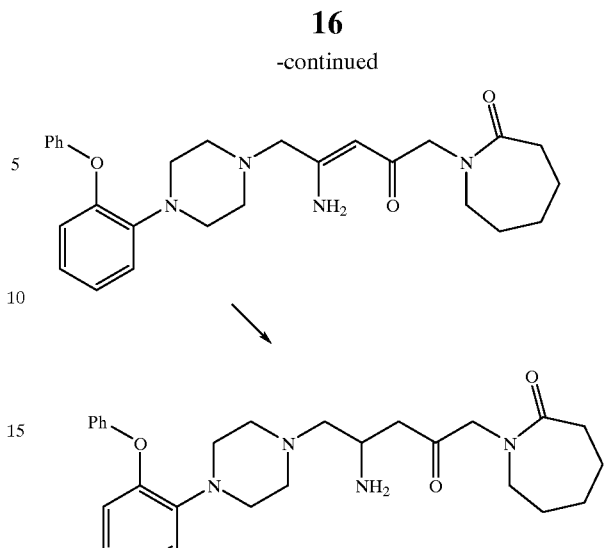

Scheme 10 may be used to produce compounds where A is

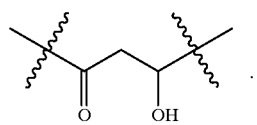

The ketone 10a is treated with LDA in an inert solvent at −78° C. for about 2 h and this mixture is treated with the aldehyde 10b to give the desired alcoholic compound of the invention. This alcohol may be dehydrated by treatment with methanesulfonyl chloride, DMAP and an organic base over several hours at about room temperature to give the unsaturated products. In order to produce the regioisomer of the illustrated products, the starting materials are modified by preparing the ketone functionality on the piperazine containing starting material; and preparing an aldehyde on the cyclic lactam piece. With respect to other modifications of the generic structure, the same methods which were used in previous schemes, may be incorporated into Scheme 10.

Scheme 10

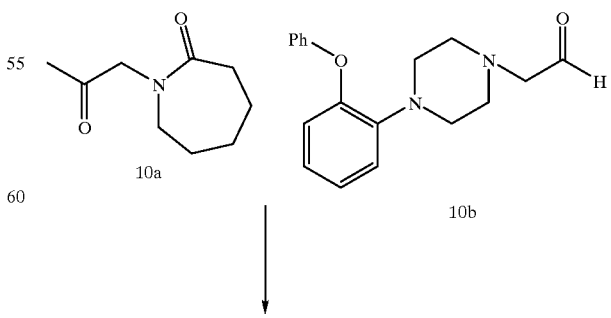

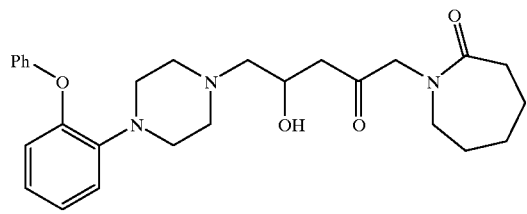
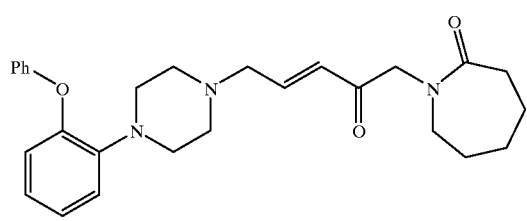
Although the claimed compounds are useful as antagonists of a 1α-AR, some compounds are more active that others and are either preferred or particularly preferred. The preferred compounds of the invention include:
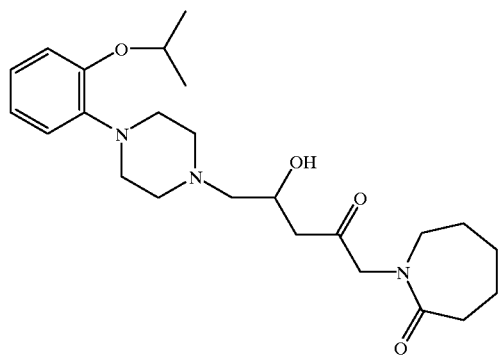
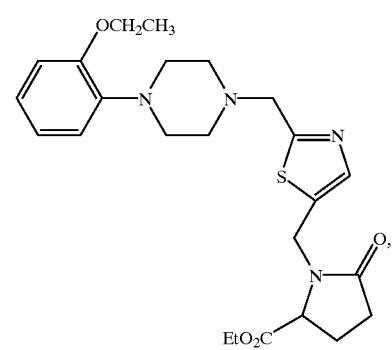
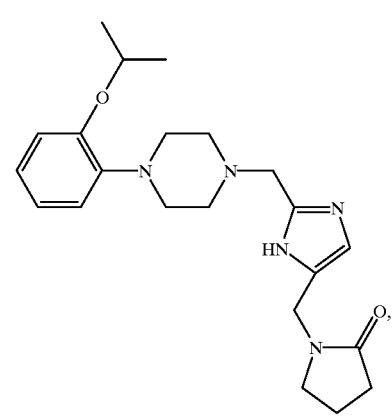
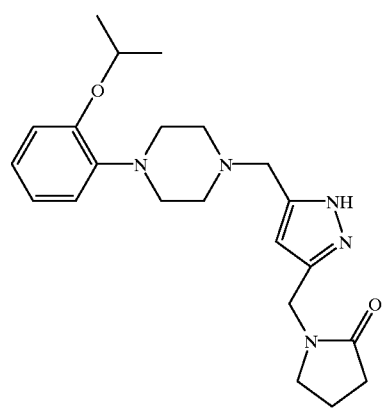
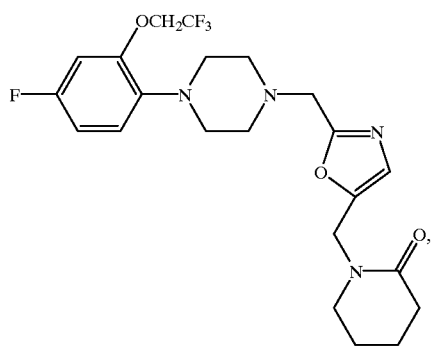

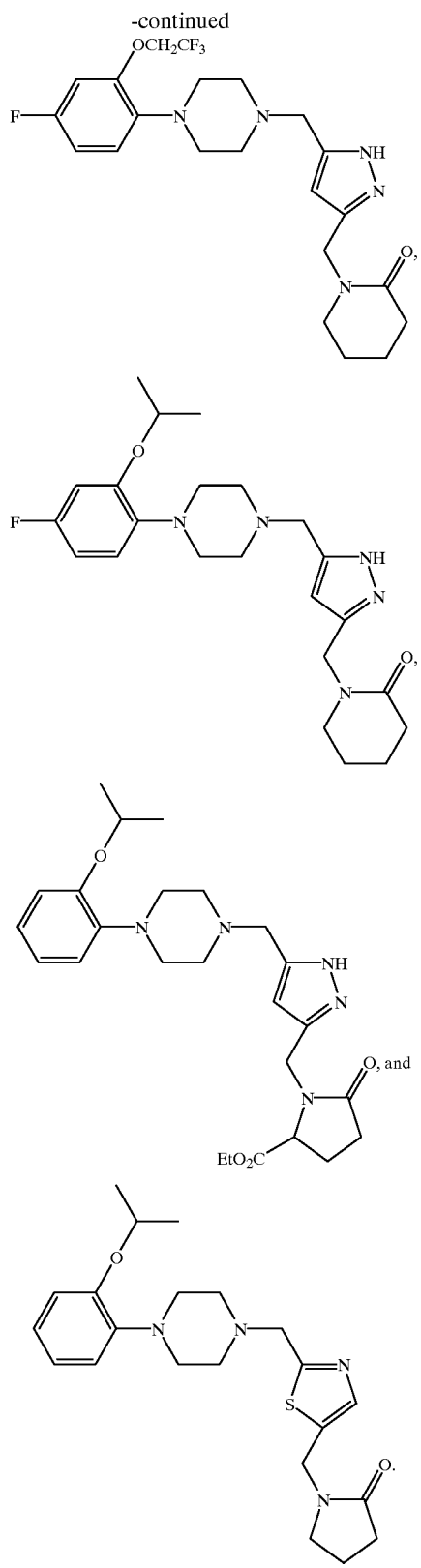

The particularly preferred compounds of Formula I include compounds where:
$R_1$ is hydrogen,
$R_2$ is $C_{1-6}$alkyl, phenyl or substituted phenyl,
$R_3$ is hydrogen,
$R_4$ is hydrogen,
A is A is ; or B is oxygen,
Z is $(CH_2)_n$ and
n is 1–4.

As indicated by the biological activity, the compounds of Formula I may be used in pharmaceutical compositions to treat patients (humans and other primates) with disorders related to inhibiting the activity of the α1a adrenergic receptor. The preferred route is oral administration, however compounds may be administered by intravenous infusion. Oral doses range from about 1–100 mg/kg daily. Infusion doses can range from about 0.01–1 mg/kg/min of inhibitor, admixed with a pharmaceutical carrier over a period ranging from several minutes to several days.

The pharmaceutical compositions can be prepared using conventional pharmaceutical excipients and compounding techniques. Oral dosage forms may be elixirs, syrups, capsules tablets and the like. Where the typical solid carrier is an inert substance such as lactose, starch, glucose, methyl cellulose, magnesium sterate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

Typically the compounds of Formula I are isolated and used as free bases, however the compounds may be isolated and used as their pharmaceutically acceptable salts. Examples of such salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic.

Aside from their biological activity, the compounds of the invention where A is

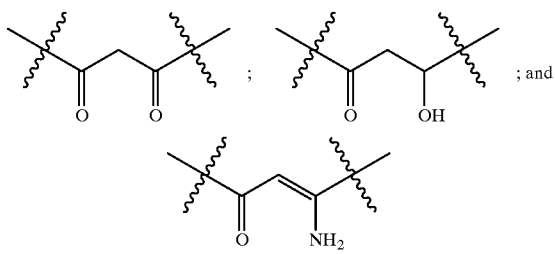

are useful as intermediates in the manufacture of other compounds of the invention.

In order to illustrate the invention the following examples are included. These examples do not limit the invention. They are meant only to suggest a method of practicing the invention. Those skilled in the art may find other methods of practicing the invention, which are obvious to them. However those methods are deemed to be within the scope of this invention.

PREPARATIVE EXAMPLES

Example 1

Cpd. 1

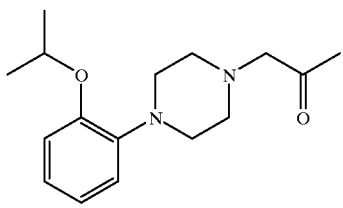

Chloroacetone (3.8 mL, 48.2 mmol) and K$_2$CO$_3$ (10.0 g, 72.4 mmol) were added to a solution of 1-(2-isopropoxyphenyl)piperazine (10.6 g, 48.2 mmol) and the resulting mixture was heated at reflux for 1 day. The mixture was filtered, and the filtrate was concentrated in vacuo to yield the title compound as a solid which was used without purification: $^1$HNMR (300 MHz, CDCl$_3$) d 6.91 (m, 4H), 4.59 (m, 1H), 3.25 (s, 2H), 3.15 (bt, 4H), 2.67 (bt, 4H), 2.19 (s, 3H), 1.34 (d, 6H, J=6.03 Hz); MS m/z 277 (MH+).

Example 2

Cpd. 2

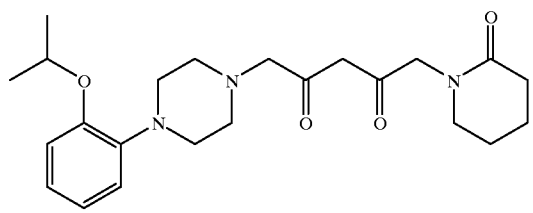

A solution of compound 1 (1.95 g, 7.0 mmol) and 1-(ethoxycarbonylmethyl)-2-piperdone (2.61 g, 14.1 mmol) in THF (10.0 mL) was slowly added to a suspension of sodium hydride (95% tech. 356.0 mg, 14.0 mmol) in THF (20.0 mL). MeOH was added in catalytic amount and the mixture was stirred at room temperature under N$_2$ for 4 h. The resulting mixture was quenched with sat. aq. NH$_4$Cl and extracted with ethyl acetate. The combined organic layer was dried (Na$_2$SO$_4$), filtered and concentrated in vacuo. The residue was purified by MPLC on silica gel using CH$_2$Cl$_2$/MeOH/triethylamine (95:3:2) as an eluent to give compound 2 as an oil: $^1$HNMR (300 MHz, CDCl$_3$) d 6.91 (m, 4H), 4.59 (m, 1H), 4.26 & 4.18 (2s, 2H), 3.69 & 3.30 (2s, 2H), 3.35 (m 2H), 3.20 (bs, 2H), 3.14 (bs, 4H), 2.69 (m, 4H), 2.46 (m, 2H), 1.86 (m, 4H), 1.34 (2d, 6H, J=6.06 Hz); MS m/z 416 (MH+). The activity of compound 2 in the α1a, α1b and α1c screens was 417, >10000 and 6043 nm respectively.

Example 3

Cpd. 3

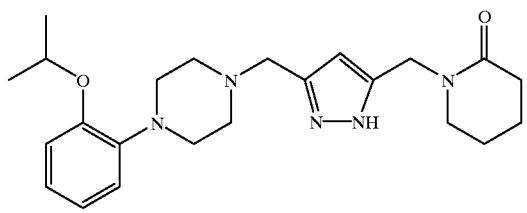

The mixture of compound 2 (572.0 mg, 1.4 mmol) and hydrazine monohydrate (103.0 mg, 2.1 mmol) in ethanol was stirred at room temperature for 3 h. The solvent was removed in vacuo, and the residue was purified by MPLC on silica gel using 3% MeOH/CH$_2$Cl$_2$ as an eluent to give the title compound, compound 3, as a solid: $^1$HNMR (300 MHz, CDCl$_3$) δ 6.91 (m, 4H), 6.17 (s, 1H), 4.59 (m, 1H), 4.48 (s, 2H), 3.61 (s, 2H), 3.34 (m, 2H), 3.12 (bs, 4H), 2.67 (bs, 4H), 2.42 (m, 2H), 1.78 (m, 4H), 1.34 (d, 6H, J=6.10 Hz); MS m/z 412 (MH+).

Example 4

Cpd. 4

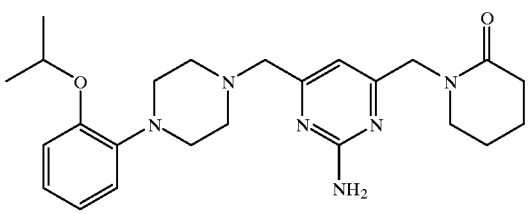

The mixture of compound 3 (119 mg, 0.29 mmol), guanidine hydrochloride (109 mg, 1.15 mmol) and sodium acetate (238 mg, 2.90 mmol) in ethanol (20.0 mL) was heated at 50° C. for 1 day. The solvent was removed in vacuo, and the residue was dissolved in ethyl acetate and washed with successive portions of water. The organic layer was dried (NaSO$_4$), filtered and the filtrate was concentrated in vacuo. The residue was purified by MPLC on silica gel using 3–5% MeOH/CH$_2$Cl$_2$ as an eluent to give compound 4 the title compound as an oil: $^1$HNMR (300 MHz, CDCl$_3$) δ 6.91 (m, 4H), 6.70 (s, 1H), 5.07 (bs, 2H), 4.59 (m, 1H), 4.50 (s, 2H), 3.48 (s, 2H), 3.34 (m, 2H), 3.14 (bs, 4H), 2.66 (bs, 4H), 2.49 (m, 2H), 1.85 (m, 4H), 1.34 (d, 6H, J=6.06 Hz); MS m/z 439 (MH+).

Example 5

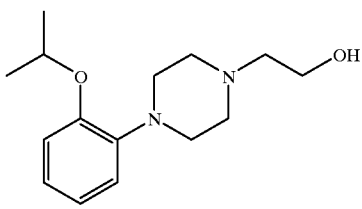

Cpd. 5

Bromoethanol (2.1 mL, 29.0 mmol) and K$_2$CO$_3$ (4.6 g, 33.5 mmol) were added to a solution of N-1-(2-isopropoxyphenyl)piperazine (4.9 g, 22.3 mmol) in acetonitrile (100 mL) and the resulting mixture was heated at reflux for 2 days. The mixture was filtered, and the filtrate was concentrated in vacuo. The residue was purified by MPLC on silica gel using 50% EtOAc/hexanes as an eluent to give compound 5 as an oil: $^1$HNMR (300 MHz, CDCl$_3$) δ 6.91 (m, 4H), 4.59 (m, 1H), 3.68 (t, 2H, J=5.43 Hz), 3.27 (bs, 1H), 3.12 (bs, 4H), 2.68 (bs, 4H), 2.60 (t, 2H, J=5.40 Hz), 1.34 (d, 6H, J=6.03 Hz; MS m/z 265 (MH+).

Example 6

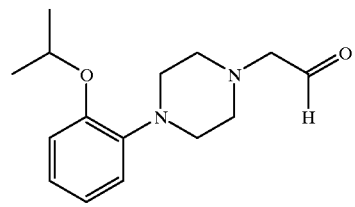

Cpd. 6

A solution of DMSO (0.74 g, 9.5 mmol) in CH$_2$Cl$_2$ (5.0 mL) was added slowly to a stirred solution of oxalyl chloride (0.66 mL, 7.6 mmol) in THF at −78° C. under nitrogen and the resulting mixture was stirred for 30 min. A solution of compound 5 (1.0 g, 3.8 mmol) in CH$_2$Cl$_2$ (10 mL) was added and the mixture was stirred at −78° C. for 5 h. Triethylamine (4.2 g, 42.0 mmol) was added and the mixture was allowed to warm to room temperature. After 30 min, water (100 mL) was added and the mixture was extracted with CH$_2$Cl$_2$. The combined organic layer was dried (NaSO$_4$), filtered, and the filtrate was concentrated in vacuo to give compound 6 as an oil without further purification.

Example 7

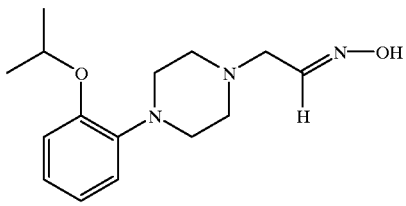

Cpd. 7

Pyridine (1.5 g, 19.0 mmol) was added slowly to a solution of compound 6 (1.1 g, 3.8 mmol) and hydroxylamine hydrochloride (0.26 g, 3.7 mmol) in ethanol (30 mL). The resulting mixture was stirred at room temperature overnight and the solvent was removed in vacuo. The residue was dissolved in EtOAc and washed with successive portions of water. The organic layer was dried (NaSO$_4$), filtered and the filtrate was concentrated in vacuo to give compound 7 as an oil without further purification: HNMR (300 MHz, CDCl$_3$) δ 7.55 (t, 1H, J=6.06 Hz), 6.91 (m, 4H), 4.59 (m, 1H), 3.72 (dd, 1H, J=7.02 Hz), 3.23 (d, 1H, J=6.08 Hz), 3.15 (m, 6H), 2.73 (bs, 4H), 1.34 (d, 6H, J=6.08 Hz); MS m/z 278 (MH+).

Example 8

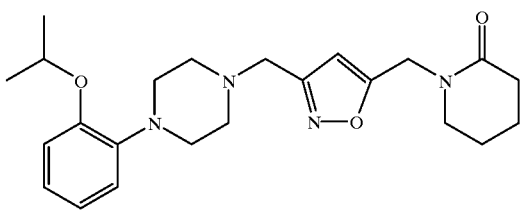

Cpd. 8

Aqueous NaOCl (11.4 mL, 7.9 mmol) and triethylamine (0.04 mL, 0.3 mmol) were added in 4 portions separately over 40 h to a stirred solution of compound 7 (190.5 mg, 0.7 mmol) and N-propargyl δ-valerolactam (140.0 mg, 1.0 mmol) in CH$_2$Cl$_2$ (15 mL) and the mixture was stirred at room temperature over this period. The mixture was poured into water and extracted with ether. The combined The organic layer was dried (NaSO$_4$), filtered and the filtrate was concentrated in vacuo. The residue was purified by MPLC on silica gel eluting with EtOAc to give the title compound as an oil; $^1$HNMR (300 MHz, CDCl$_3$) δ 6.91 (m, 4H), 6.26 (s, 1H), 4.67 (s, 2H), 4.59 (m, 1H), 3.64 (s, 2H), 3.41 (t, 2H, J=5.65 Hz), 3.12 (bs, 4H), 2.68 (bs, 4H), 2.43 (t, 2H, J=5.65), 1.83 (m, 4H), 1.34 (d, 6H, J=6.04 Hz); MS m/z 413 (MH+).

Example 9

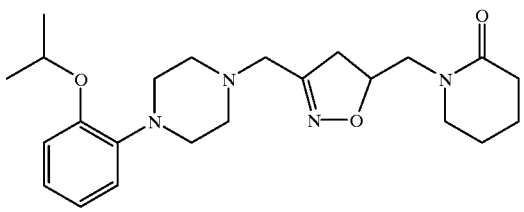

Cpd. 9

Aqueous NaOCl (11.4 mL, 7.9 mmol) and triethylamine (0.04 mL, 0.3 mmol) were added in 4 separate portions over 40 h to a stirred solution of compound 7 (200.0 mg, 0.7 mmol) and N-allyl δ-Valerolactam (150.0 mg, 1.1 mmol) in CH$_2$Cl$_2$ (15 mL) at room temperature. The mixture was poured into water and extracted with ether. The combined organic layer was dried (NaSO$_4$), filtered and the filtrate was concentrated in vacuo. The residue was purified by MPLC on silica gel eluting with 70% EtOAc/hexanes to give the title compound as an oil: $^1$HNMR (300 MHz, CDCl$_3$) δ 6.91 (m, 4H), 4.86 (m, 1H), 4.59 (m, 1H), 3.87 (dd, 1H, J=3.33 Hz), 3.57 (m, 1H), 3.41 (m, 1H), 3.30 (s, 2H), 3.17 (m, 2H), 3.11 ((bs, 4H), 2.84 (dd, 1H, J=7.58 Hz), 2.63 (t, 4H, J=3.28

Hz), 2.40 (m, 2H), 1.79 (m, 4H), 1.34 (d, 6H, J=6.06 Hz); MS m/z 415 (MH+).

Example 10

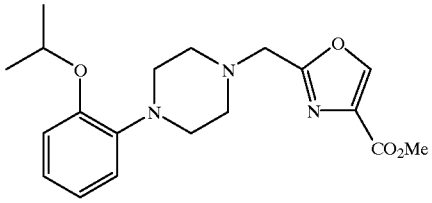

Cpd. 10

1-(2-Isopropoxyphenyl)piperazine (1.3 g, 6.0 mmol), 2-bromomethyl-3-carbomethoxyoxazole (1.2 g, 5.4 mmol), and diisopropylethylamine (1.4 mL, 8.1 mmol) were combined in THF (25 mL) and heated to reflux (3 h). The reaction mixture was cooled to room temperature, diluted with ethyl acetate (50 mL), washed with water and brine. The combined organic extracts were dried (Na$_2$SO$_4$), and concentrate to a crude oil. Purification by flash silica gel chromatography using hexane/ethyl acetate/triethylamine [13:6:1] as an eluent compound 10 as a yellow glass: $^1$HNMR (300 MHz, C$_6$D$_6$) d; LCMS (CI) m/z (M$^+$+1)

Example 11

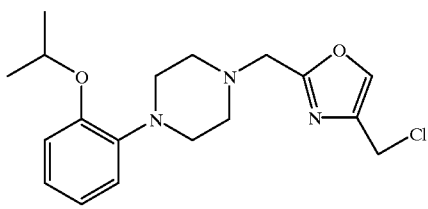

Cpd. 11

A solution of compound 10 (379 mg, 1.05 mmol) in absolute ethanol (15 mL) was combined with NaBH$_4$ (95 mg, 2.5 mmol) and heated at reflux for 1 h. The reaction mixture was cooled to room temperature, quenched with water (35 mL) and adjusted to pH<4 using 1N HCl . The reaction mixture was subsequently adjusted to a pH>6 with sat. NaHCO$_3$ and extracted (3×) with ether/ethyl acetate (1:1). The organic extracts were combined, washed with water and brine, dried (Na$_2$SO$_4$), and concentrated in vacuo to give the crude alcohol as a colorless oil: $^1$HNMR (300 MHz, C$_6$D$_6$) δ 7.03 (s, 1H); 6.86–6.91 (m, 2H); 6.75–6.80 (m, 2H); 4.43 (s, 2H); 4.32 (septet, J=6.0 Hz, 1H); 3.49 (s, 2H); 3.07 (br m, 4H); 2.59 (br m, 4H); 1.12 (d, J=6.0 Hz, 6H); LCMS (CI) m/z 332 (M$^+$+1). The crude alcohol (210 mg, 0.63 mmol) in CH$_2$Cl$_2$ (4 ml) was combined with thionyl chloride (1.0 mL, 13.5 mmol) and allowed to stir (16 h). The solvent and excess thionyl chloride were removed in vacuo and the residue was concentrated from benzene (2×). The remaining salts were partitioned between CH$_2$Cl$_2$ and aqueous NaHCO$_3$. The organic layer was separated, washed with brine, dried (Na$_2$SO$_4$), and concentrated to give 200 mg (57%) of 11 as a tan oil: $^1$HNMR (300 MHz, C$_6$D$_6$) δ 6.87–6.92 (m, 2H); 6.85 (s, 1H); 6.74–6.79 (m, 2H); 4.31 (septet, J=6.0 Hz, 1H); 4.05 (s, 2H); 3.42 (s, 2H); 3.04 (br m, 4H); 2.56 (br m, 4H); 1.12 (d, J=6.0 Hz, 6H); LCMS (CI) m/z 350 (M$^+$+1).

Example 12

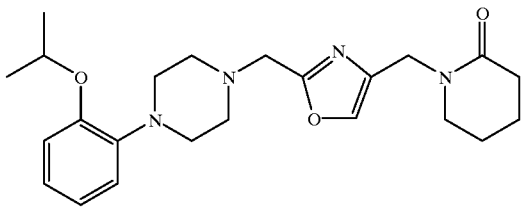

Cpd. 12

δ-Valerolactam (86 mg, 86 mmol) was added to an ice cold suspension of potassium hydride (44 mg, 1.12 mmol) in THF (4 mL) and stirred for 15 min. A solution of compound 11 (50 mg, 0.14 mmol) in DMF (2 mL) was added to this mixture and the resulting mixture was allowed to stir overnight. The reaction mixture was carefully quenched with water (25 mL) and extracted (3×) with ether/ethyl acetate [1:1]. The combined extracts were washed with water (5×) and brine, dried (Na$_2$SO$_4$), and concentrated to crude oil. Purification by flash silica gel chromatography using ethyl acetate/triethylamine [19:1] as an eluent provided compound 12, the title compound as a colorless glass: $^1$HNMR (300 MHz, C$_6$D$_6$) δ 7.40 (s, 1H); 6.85–6.93 (m, 2H); 6.75–6.80 (m, 2H); 4.41 (s, 2H); 4.32 (septet, J=6.0 Hz, 1H); 3.50 (s, 2H); 3.05 (br m, 6H); 2.60 (br m, 4H); 2.15 (br m, 2H); 1.14–1.34 (m, 4H); 1.12 (d, J=6.0 Hz, 6H); LCMS (CI) m/z 413 (M$^+$+1).

Example 13

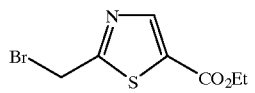

Cpd. 13

N-bromosuccinimide (2.58 g, 14.5 mmol) and AIBN (158 mg, 0.965 mmol) were added to a stirred solution of 2-methyl-5-(carboethoxy)thiazole (1.65 g, 9.65 mmol) in CCl$_4$ (40 mL). The mixture was stirred at 80° C. for 5 h, an additional portion of AIBN (158 mg, 0.965 mmol) was added and the resulting mixture was stirred for another 16 h at 80° C. The mixture was cooled, filtered thru celite and the filtrate was concentrated in vacuo. The residue was purified by column chromatography on silica gel using CH$_2$Cl$_2$/hexane as an eluent to give compound 13 (1.09 g, 13%) gas a dark-red oil: MS (ES): 250 (MH$^+$).

Example 14

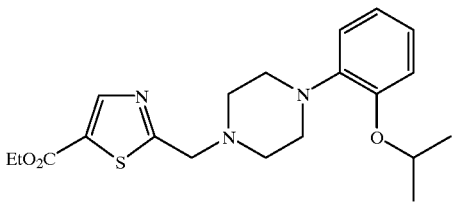

Compound 14

The fumarate salt of 4-(2-isopropyloxyphenyl)piperazine (2.78 g, 8.5 mmol) was basified with 20% NaOH (70 mL)

and extracted with CH$_2$Cl$_2$. The combined organic layer was dried (Na$_2$SO$_4$), and concentrated in vacuo to give a yellowish oil. A mixture of the yellowish oil, compound 13 (1.94 g, 7.76 mmol) and triethylamine (1.57 g, 15.52 mmol) in 1-methyl-2-pyrrolidinone (15 mL) was stirred at 85° C. for 21 h and quenched with water. The resulting organic layer was extracted with ether, dried (Na$_2$SO$_4$) and concentrated in vacuo. The product was purified by column chromatography on silica gel EtOAc/hexane to give compound 14 as a red oil (2.27 g, 69%): MS (ES): 390 (MH$^+$).

Example 15

Cpd. 15

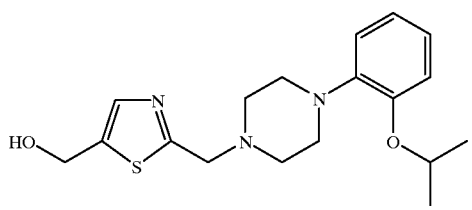

A mixture of compound 14 (2.27 g, 5.8 mmol) and sodium borohydride (1.1 g, 29 mmol) was stirred at 78° C. for 5 h. Water was added and the mixture was acidified to pH 7 with 1 N HCl (aq). The aqueous mixture was extraced with several portions of ether and the combined organic extracts were dried (Na$_2$SO$_4$) and concentrated in vacuo. The residue was purified by column chromatography on silica gel CH$_2$Cl$_2$/acetone to give compound 15 (1.64 g, 81%) as yellow-brown oil: MS (ES): 348 (MH$^+$)

Example 16

Cpd. 16

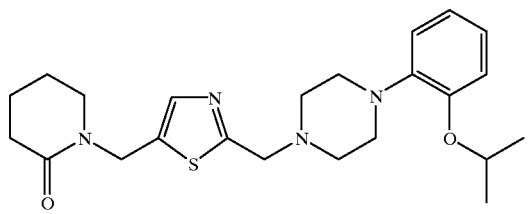

A mixture of compound 15 (1 g, 2.9 mmol) and thionyl chloride (1.7 g, 14.3 mmol) in CH$_2$Cl$_2$ (5 mL) was stirred at 20° C. for 20 h. Ice was added and the mixture was basified to a pH of 7–8 by the dropwise addition of NaHCO$_3$(aq). The resulting aqueous layer was extracted with CH$_2$Cl$_2$ and the combined organic extracts were dried (Na$_2$SO$_4$) and concentrated in vacuo to the crude chloride as a dark-red oil: MS (ES): 368 (MH$^+$)

The δ-valerolactam (344 mg, 3.47 mmol) was dissolved in THF (10 mL) and treated with n-BuLi (2.2 mL, 1.6 M, 3.5 mmol) at 20° C. for 15 min. A solution of the crude chloride (850 mg, 2.32 mmol) in DMF (2 mL) was added and the resulting mixture was stirred at 80° C. for 20 h. The reaction mixture was partitioned between water and ether. The organic extracts dried (Na$_2$SO$_4$) and concentrated in vacuo. The residue was purified by column chromatography on silica gel EtOAc/hexane to give compound 16 as yellow-brown oil: MS (ES): 429 (MH$^+$).

Example 17

Cpd. 17

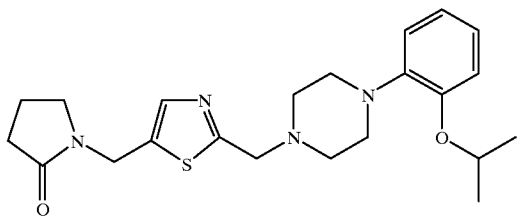

2-Pyrrolidinone (30 mg, 0.36 mmol) was dissolved in THF (2 mL) and treated with n-BuLi (0.23 mL, 1.6 M, 0.36 mmol) at 20° C. for 15 min. A solution of the crude chloride (87 mg, 0.24 mmol) in DMF (1 mL) was added and the mixture was stirred at 80° C. for 3 h. The resulting mixture was partitioned between water and the aqueous layer was extracted with several portions of ether. The combined organic extracts were dried (Na$_2$SO$_4$) and concentrated in vacuo. The residue was purified by column chromatography on silica gel EtOAc/hexane to give compound 17 (18 mg, 18%) as yellow oil: MS (ES): 415 (MH$^+$).

Example 18

Cpd. 18

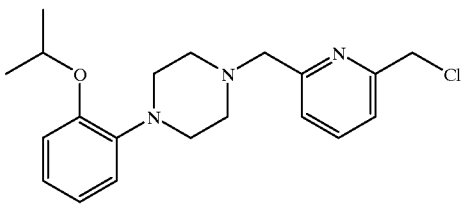

1-(2-Isopropoxyphenyl)piperazine 2.0 g (5.9 mmol) was treated with 2,6-bis(chloromethyl)pyridine (3.1 g, 17.8 mmol) and triethylamine (11.9 mmol). The resulting brownish solution was heated at reflux in THF (anhydrous) 40 ml for 3 h. The solution was cooled and treated with conc. HCl, (1 mL) ether and water (10 mL). The product was extracted into the aqueous layer, basified (sat NaHCO$_3$), and extracted into ether. The combined organic extracts were concentrated. in vacuo to give compound 18 as a syrup 0.98 g (47%).

Example 19

Cpd. 19

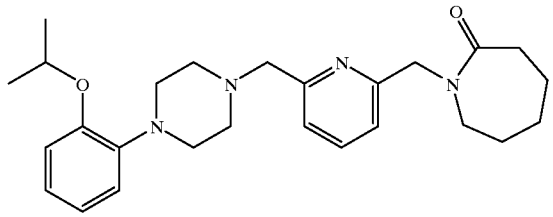

A solution of ε-caprolactam (95 mg, 0.8 mmol) in anhydrous THF (1 mL) was treated with 1.6 M n-BuLi (0.5 mL, 0.8 mmol) at 0° C. under $N_2$. The resulting suspension was treated with a solution of compound 18 (215 mg, 0.6 mmol) in anhydrous DMF(1 ml), heated at reflux for 2 h and cooled. The resulting mixture was treated with water and extracted into ether. The combined organic layers were dried ($Na_2SO_4$) and concentrated in vacuo. The residue was purified by flash chromatography on silica gel using varying concentration of $CH_2Cl_2$/MeOH (50:1, 40:1, 30:1, 20:1) to give compound 19 (0.176, 68%): MS m/z 437 $MH^+$; $H^1$ NMR ($CDCl_3$) δ 7.62 (t, J=7.7 Hz, 1H), 7.35 (d, J=7.4 Hz, 1H), 7.16 (d, J=7.6 Hz, 1H), 6.89 (m 4H), 4.72 (s, 2H), 4.59(q, J=12 Hz, 1H), 3.71 (s, 2H), 3.42 (m, 2H), 3.14 (brs 4H), 2.69 (brs, 4H), 2.62 (s, 2H), 1.71 (s, 6H), 1.33 (d, J=5.99 Hz, 6H).

Example 20

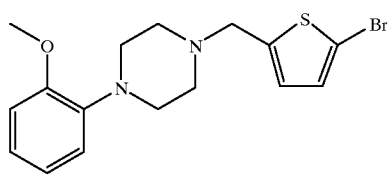

Cpd. 20

Glacial AcOH (1.8 mL, 31.4 mmol) and $NaBH(OAc)_3$ (8.65 g, 40.8 mmol) were successively added to a stirred solution of 1-(2-methoxyphenyl)piperazine (6.4 g, 31.4 mmol) and 5-bromo-2-thiophenecarboxaldehyde (6.0 g, 31.4 mmol) in $CH_2Cl_2$ at room temperature. The mixture was stirred for 4 h and partitioned between ether and satd. $Na_2CO_3$. This mixture was extracted with several portions of ether and the combined organic extracts were washed with brine, dried ($Na_2SO_4$), and concentrated. The residue was flushed through a short silica gel plug eluting with EtOAc to obtain compound 20: $^1$HNMR (300 MHz, $CDCl_3$) δ (ppm) 6.84–7.03 (m, 5H), 6.68 (d, J=3.6 Hz, 1H), 3.85 (s, 3H), 3.71 (s, 2H), 3.09 (bs, 4H), 2.69 (bs, 4H); MS m/z 367 ($MH^+$) and 369 ($MH^+$)

Example 21

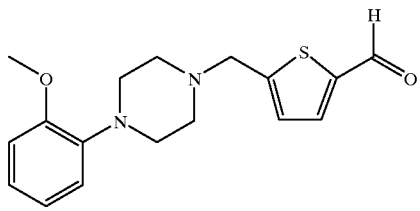

Cpd. 21

1.7M t-Butyllithium (7.9 mL, 13.4 mmol) was added to a solution of compound 20 (4.1 g, 11.2 mmol) in THF at −78° C. DMF (2.0 mL, 25.8 mmol) was added after 1 h and the resulting mixture was stirred for another 6 h at −78° C. The reaction mixture was warmed to 0° C., quenched by addition of satd. $NH_4Cl$ and extracted with ethyl acetate. The combined organic extracts were washed with brine, dried ($Na_2SO_4$), and concentrated in vacuo. The material was flushed through a short silica gel plug and eluted with EtOAc to afford compound 21: $^1$HNMR (300 MHz, $CDCl_3$) δ (ppm) 9.85 (s, 1 h), 7.64 (d, J=3.7 Hz, 1H), 7.06 (d, J=3.7 Hz, 1H), 6.84–7.01 (m, 4H), 3.85 (s, 3H), 3.81 (s, 2H), 3.11 (bs, 4H), 2.73 (t, J=4.5 Hz, 4H); MS m/z 317 ($MH^+$).

Example 22

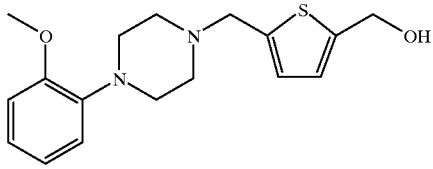

Cpd. 22

$NaBH_4$ (1.26 g, 34.1 mmol) was added portionwise to a solution of the above compound 21 (3.6 g, 11.4 mmol) in MeOH at ambient temperature. The solvent was removed after 0.5 h and sat'd. $NH_4Cl$ was added to the residue. The aqueous layer was extracted with EtOAc, and the combined organic extracts were washed with brine, dried ($Na_2SO_4$), and concentrated in vacuo. The residue was was purified by flash chromatography on silica gel using ethyl acetate/hexanes (20–30% EtOAc in hexanes) as an eluent to give compound 21: $^1$HNMR (300 MHz, $CDCl_3$) δ (ppm) 6.79–7.02 (m, 6H), 4.77 (s, 2H), 3.85 (s, 3H), 3.75 (s, 2H), 3.09 (bs, 4H), 2.70 (bs, 4H), 1.99 (bs, 1H); MS m/z 319 ($MH^+$).

Example 23

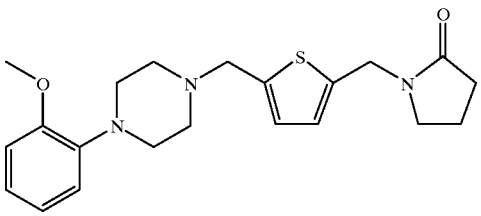

Cpd. 23

$SOCl_2$ (3.0 mL, excess) was added to compound 22 (0.182 g, 0.57 mmol) in $CH_2Cl_2$ (5.0 mL). The reaction was stirred for 6 h and concentrated in vacuo to give the crude chloro derivative. In a separate flask pyrrolidinone (0.098 g, 1.16 mmol) was added slowly to a suspension of NaH (0.055 g, 2.3 mmol) in DMF. After 0.5 h a solution of the chloro derivative in DMF (1.0 mL) was injected dropwise to the later. The resulting mixture was stirred for 18 h, quenched by the addition of sat'd. $NH_4Cl$ and extracted with EtOAc. The combined extracts were successively washed with water and brine, dried ($Na_2SO_4$), and concentrated in vacuo. The residue was purified by column chromotography on silica gel chromatography using EtOAc/hexanes (10–25%) to give compound 23 $^1$HNMR (300 MHz, $CDCl_3$) δ (ppm) 6.77–7.00 (m, 6H), 4.57 (s, 2H), 3.85 (s, 3H), 3.74 (s, 2H), 3.37 (t, J=7.0 Hz, 2H), 3.10 (bs, 4H), 2.69 (bs, 4H), 2.42 (t, J=8.1 Hz, 2H), 2.01 (quin, J=7.5 Hz, 2H); MS m/z 386 ($MH^+$)

Example 24

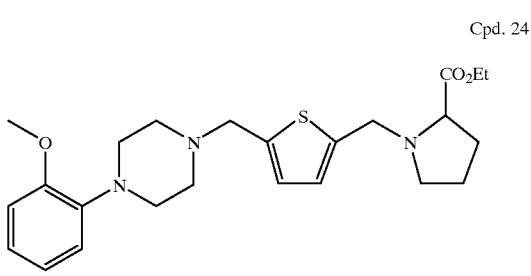

Cpd. 24

Et$_3$N (1.05 mL, 7.5 mmol) and NaBH(OAc)$_3$ (1.73 g, 8.2 mmol) were successively added to a stirred solution of compound 21 (2.0 g, 6.3 mmol) and L-proline methyl ester hydrochloride (1.04 g, 6.3 mmol) in CH$_2$Cl$_2$ at room temperature. After 6 h the reaction mixture was quenched with sat'd. Na$_2$CO$_3$, and extracted with CH$_2$Cl$_2$. The combined organic extracts were washed with brine, dried (Na$_2$SO$_4$), and concentrated. The residue was purified by flash chromotography on silica gel using EtOAc/hexanes [10–20%] to give compound 24: $^1$HNMR (300 MHz, CDCl$_3$) δ (ppm) 6.78–7.02 (m, 4H), 6.76 (d, J=3.4 Hz, 1H), 6.74 (d, J=3.4 Hz, 1H), 4.03 (d, J=14.0 Hz, 1H), 3.86 (d, J=14.0 Hz, 1H), 3.85 (s, 3H), 3.74 (s, 2H), 3.70 (s, 3H), 3.33 (dd, J=5.8 Hz, 8.7 Hz, 1H), 3.10 (bm, 5H), 2.70 (bs, 4H), 2.55 (dd, J=6.5 Hz, 8.0 Hz, 1H), 1.61–2.18 (m, 4H); MS m/z 430 (MH$^+$).

Example 25

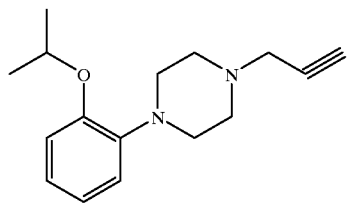

Cpd. 25

Propargyl bromide (80 wt. % in toluene; 9.4 mL, 84.0 mmol) was added to a mixture of 1-(2-isopropoxyphenyl)piperazine (15.4 g, 70.0 mmol) and K$_2$CO$_3$ (12.58 g, 91.0 mmol) in CH$_3$CN, and heated at 65° C. for 24 h. The reaction mixture was concentrated and purified by flash chromotography on silica gel using 5–10% EtOAc/hexanes as an eluent to give compound 25. $^1$HNMR (300 MHz, CDCl$_3$) δ (ppm) 6.85–6.98 (m, 4H), 4.60 (sept, J=6.1 Hz, 1H), 3.36 (d, J=2.4 Hz, 2H), 3.16 (bs, 4H), 2.76 (t, J=4.6 Hz, 4H), 2.28 (t, J=2.4 Hz, 1H), 1.34 (d, J=6.1 Hz, 6H); MS m/z 259 (MH$^+$).

Example 26

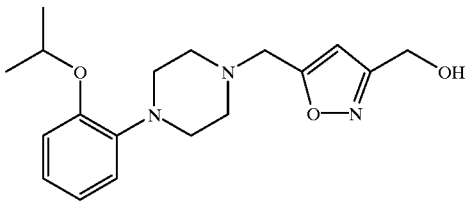

Cpd. 26

Et$_3$N (0.8 mL, 5.6 mmol) was injected slowly to a flask containing compound 25 (14.5 g, 56.1 mmol), 2-(2-nitroethoxy)tetrahydropyran (14.8 g, 84.2 mmol) and PhNCO (24.4 mL, 224.5 mmol) in toluene. The reaction mixture was heated at 62° C. for 32 h and cooled to ambient temperature. Water (10.0 mL) was added and the resutling mixture was stirred for 2 h. The solid by-product was removed by filtration and the filtrate was concentrated to obtain a dark viscous material which was used without further purification.

The dark material was dissolved in ether (80 mL) and stirred with 1N HCl (100 mL) for 2 h. The reaction was then neutralized with sat'd. Na$_2$CO$_3$ and extracted with EtOAc. The combined organic extracts were washed with brine, dried (Na$_2$SO$_4$), and concentrated. The residue was purified by flash chromatography on silica gel using 20–50% EtOAc/hexanes as an eluent to give compound 26: $^1$HNMR (300 MHz, CDCl$_3$) δ (ppm) 6.84–6.98 (m, 4H), 6.29 (s, 1H), 4.76 (s, 2H), 4.59 (sept, J=6.1 Hz, 1H), 3.75 (s, 2H), 3.14 (bs, 4H), 2.72 (t, J=4.6 Hz, 4H), 2.22 (bs, 1H), 1.34 (d, J=6.1 Hz, 6H); MS m/z 332 (MH$^+$).

Example 27

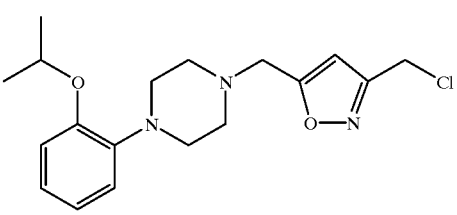

Cpd. 27

Thionyl chloride (3.0 mL, excess) was added to compound 26 (0.4 g, 1.2 mmol) in CH$_2$Cl$_2$ (5.0 mL) and the reaction was stirred for 6 h at ambient temperature. The volatile components were then removed in vacuo. The residue was dissloved in EtOAc and neutralized with 10% NaHCO$_3$. The organic layer was successively washed with water and brine, dried (Na$_2$SO$_4$), and concentrated. Evaporated the solvent and toluene were added to the residue and the solution was concentrated in vacuo to give compound 27, which was used without further purification: $^1$HNMR (300 MHz, CDCl$_3$) δ (ppm) 6.85–6.98 (m, 4H), 6.35 (s, 1H), 4.59 (s, 2H), 4.58 (sept, J=6.3 Hz, 1H), 3.76 (s, 2H), 3.14 (bs, 4H), 2.73 (bs, 4H), 1.34 (d, J=6.3 Hz, 6H).

Example 28

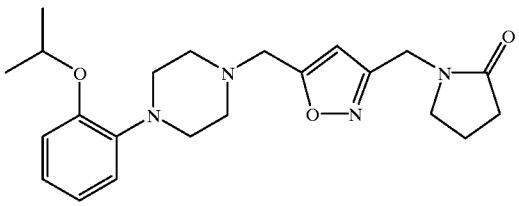

Cpd. 28

Pyrrolidinone (0.195 g, 2.3 mmol) was added slowly to a suspension of NaH (0.055 g, 2.3 mmol) in DMF. After 0.5 h a solution of cpd. 27 (1.0 mL DMF) was injected followed by addition of KI (0.02 g, cat.). Stirred for 18 h, then sat'd. $NH_4Cl$ was added and extracted with EtOAc. The combined extracts were successively washed with water and brine, dried ($Na_2SO_4$), and concentrated. The residue was purified by chromatography on silica gel using 20–30% EtOAc/hexanes) to give compound 28: $^1$HNMR (300 MHz, $CDCl_3$) δ (ppm) 6.84–6.98 (m, 4H), 6.19 (s, 1H), 4.59 (sept, J=6.0 Hz, 1H), 4.52 (s, 2H), 3.72 (s, 2H), 3.39 (t, J=7.0 Hz, 2H), 3.13 (bs, 4H), 2.70 (bs, 4H), 2.43 (t, J=8.1 Hz, 2H), 2.05 (quin, J=7.5 Hz, 2H), 1.34 (d, J=6.0 Hz, 6H): MS m/z 399 ($MH^+$).

Example 29

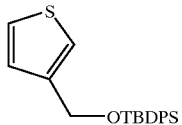

Cpd. 29 t-Butyldiphenylchlorosilane (11.3 mL, 43.3 mmol) was added to a stirred solution of 3-thiophenemethanol (4.5 g, 39.4 mmol) and imidazole (5.9 g, 86.7 mmol) in DMF at room temperature. After 24 h the reaction mixture was quenched with brine and worked up using EtOAc. The combined organic extracts were washed with brine, dried ($Na_2SO_4$) and concentrated in vacuo. The residue was purified on a silica gel pad, eluting with ether and concentrating in vacuo to give the compound 29: $^1$HNMR (300 MHz, $CDCl_3$) δ (ppm) 7.69 (m, 4H), 7.34–7.43 (m, 6H), 7.27 (dd, J=1.7 Hz, 3.1 Hz, 1H), 7.15 (dd, J=1.4 Hz, 2.6 Hz, 1H), 6.99 (dd, J=1.0 Hz, 3.6 Hz, 1H), 4.76 (s, 2H), 1.08 (s, 9H).

Example 30

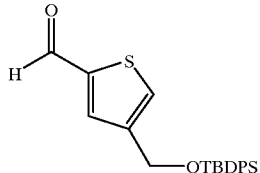

Cpd. 30 t-Butyllithium (1.7 M; 0.84 mL, 1.4 mmol) was added to a solution of 3-(t-butyldiphenylsilyloxymethyl)thiophene (0.42 g, 1.2 mmol) in THF at −78° C. DMF (0.23 mL, 3.0 mmol) was added after 1 h and stirring continued for another 6 h at −78° C. The mixture was allowed to warm to 0° C., quenched by addition of sat'd. $NH_4Cl$ and extracted with EtOAc. The combined organic extracts were washed with brine, dried ($Na_2SO_4$), and concentrated. Although the $^1$HNMR of the crude residue showed compound 30 as the predominant product along with a trace of an unidentified material, the residue was used without further purification: $^1$HNMR (300 MHz, $CDCl_3$) δ (ppm) 9.87 (s, 1H), 7.67 (dd, J=1.4 Hz, 6.0 Hz, 4H), 7.61 (d, J=0.8 Hz, 1H) 7.55 (bs, 1H), 7.36–7.44 (m, 6H), 4.74 (s, 2H), 1.09 (s, 9H) :MS m/z 381 ($MH^+$).

Example 31

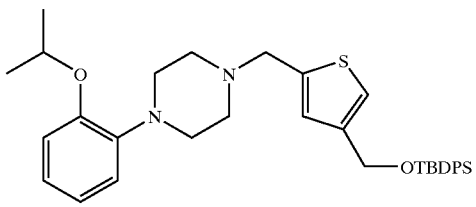

Cpd. 31

Glacial AcOH (0.55 mL, 10.0 mmol) and $NaBH(OAc)_3$ (2.76 g, 13.0 mmol) were successively added to a stirred solution of 1-(2-isopropoxyphenyl)piperazine (2.2 g, 10.0 mmol) and compound 30 (3.8 g, 10.0 mmol) in $CH_2Cl_2$ at room temperature. After 4 h the reaction mixture was quenched by slow addition of sat'd. $Na_2CO_3$ and extracted with $CH_2Cl_2$. The combined organic extracts were washed with brine, dried ($Na_2SO_4$), and concentrated. The material was flushed through a short silica gel plug eluting with EtOAc to compound 31: $^1$HNMR (300 MHz, $CDCl_3$) δ (ppm) 7.68 (d, J=7.4 Hz, 4H), 7.35–7.44 (m, 6H), 7.06 (bs, 1H), 6.84–6.94 (m, 4H), 6.81 (bs, 1H), 4.70 (s, 2H), 4.59 (sept, J=6.0 Hz, 1H), 3.72 (s, 2H), 3.13 (bs, 4H), 2.66 (bs, 4H), 1.33 (d, J=6.0 Hz, 6H), 1.08 (s, 9H); MS m/z 585 ($MH^+$).

Example 32

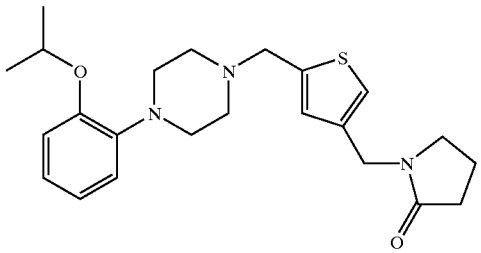

Cpd. 32

TBAF (1.0 M in THF; 11.7 mL, 11.7 mmol) was added to a solution of compound 31 (5.7 g, 9.8 mmol) in THF and the resulting mixture was stirred overnight. Brine was added and the mixture was extracted with EtOAc. The combined organic extracts were washed with brine, dried ($Na_2SO_4$), and concentrated. The residue was purified by flash chromatography on silica gel using 5–20% EtOAc/hexanes as an eluent, to give the corresponding alcohol: $^1$HNMR (300 MHz, $CDCl_3$) δ (ppm) 7.12 (s, 1H), 6.84–6.95 (m, 5H), 4.63 (s, 2H), 4.59 (sept, J=6.2 Hz, 1H), 3.74 (s, 2H), 3.12 (bs, 4H), 2.67 (bs, 4H), 1.71 (bs, 1H), 1.34 (d, J=6.2 Hz, 6H); MS m/z 347 (MH+).

SOCl$_2$ (3.0 mL, excess) was added to the alcohol (0.2 g, 0.57 mmol) in CH$_2$Cl$_2$ (5.0 mL). The reaction was stirred for 6 h then concentrated in a rotary evaporator and dried in vacuo to obtain the crude foamy chloro derivative, which was used immediately without purification.

Pyrrolidinone (0.098 g, 1.16 mmol) was added slowly to a suspension of NaH (0.055 g, 2.3 mmol) in DMF. After 0.5 h, a solution of the chloro derivative in DMF (1.0 mL) was injected to the reaction mixture and the reaction was stirred for 18 h. Sat'd. NH$_4$Cl was added and the mixture was extracted with several portions of EtOAc. The combined extracts were successively washed with water and brine, dried (Na$_2$SO$_4$), and concentrated. The product was purified by column chromatography on silica gel using 10–25% EtOAc/hexanes as an eluent to affforded compound 32: $^1$HNMR (300 MHz, CDCl$_3$) δ (ppm) 7.02 (bs, 1H), 6.84–6.91 (m, 4H), 6.84 (bs, 1H), 4.59 (sept, J=6.0 Hz, 1H), 4.39 (s, 2H), 3.72 (s, 2H), 3.31 (t, J=7.0 Hz, 2H), 3.12 (bs, 4H), 2.65 (bs, 4H), 2.43 (t, J=8.0 Hz, 2H), 2.00 (quin, J=7.5 Hz, 2H), 1.34 (d, J=6.0 Hz, 6H); MS m/z 414 (MH+)

Example 33

Cpd. 33

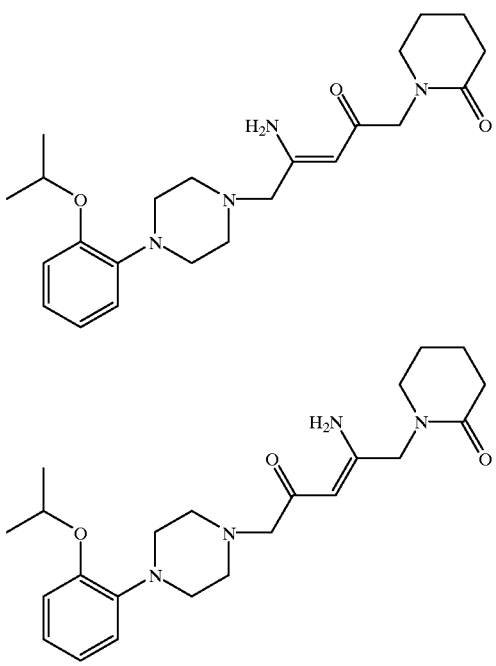

An aqueous solution of ammonium hydroxide (30%, 2.0 mL) was added to a solution of compound 2 (160 mg, 0.38 mmol) in EtOH (25.0 mL) and the resulting mixture was stirred at room temperature for 3 days. EtOH was removed under reduced pressure and the residue was taken up in ethyl acetate. This solution was washed with successive portions of water and the combined organic layer was dried (Na$_2$SO$_4$), filtered and the filtrate was concentrated in vacuo. The residue was purified by MPLC on silica gel using 3–5% MeOH in CH$_2$Cl$_2$ to afford a mixture of regioisomers as oil: $^1$HNMR (300 MHz, CDCl$_3$) d 6.91 (m, 4H), 4.59 (m, 4H), 4.15 (s, 2H), 3.33 & 3.30 (2s, 3H), 3.11 (m, 6H), 2.64 (m, 2H), 2.42 (m, 4H), 1.86 (m, 4H), 1.34 (d, 6H, J=6.06 Hz; MS m/z 415 (MH+). The activity of compound 33 in the α1a, α1b and α1c screens was 317, >10000 and 1268 nm respectively.

Example 34

Cpd. 34

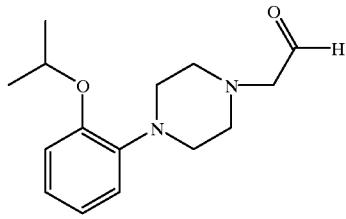

DIBAL(H) (35.0 mL, 1M solution in toluene) was slowly added to a solution of 1-(2-acetonitrile)-4-(2-isopropoxyphenyl)piperazine (6.0 g, 23.0 mmol) in toluene (50.0 mL) at –78° C. under N$_2$ and the resulting mixture was stirred at this temperature for 3 h. The mixture was then warmed to room temperature and stirred for additional 3 h. Sat. ammonium chloride solution was added and the mixture was extracted with successive portions of ethyl acetate. The combined organic layer was dried (Na$_2$SO$_4$), filtered and the filtrate concentrated in vacuo. The residue was purified by MPLC on silica gel using EtOAc/hexanes (1:1) as an eluent to give the desired aldehyde as an oil: $^1$HNMR (300 MHz, CDCl$_3$) d 9.75 (m, 1H), 6.92 (m, 4H), 4.60 (m, 1H), 3.35 (d, 2H, J=1.40 Hz), 3.17 (m, 4H), 2.72 (m, 4H), 1.34 (d, 6H, J=6.03 Hz); MS m/z 295 (MH+ of hemiacetal in MeOH).

Example 35

Cpd. 35

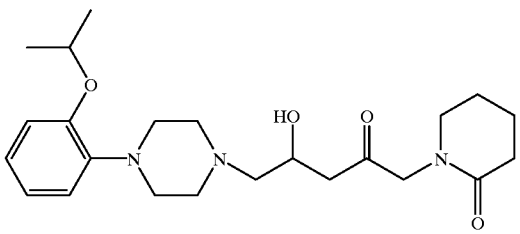

To a solution of LDA (1.6 mL, 2.5 mmol, 1.5 M solution in THF) in THF (20.0 mL) at –78° C. under N$_2$ was added slowly compound 34 (382 mg, 2.5 mmol) in THF (5.0 mL) and the mixture was stirred at this temperature for 1 h. A solution of 1-[2-oxopropyl]-2-piperidone (645 mg, 2.5 mmol) in THF (5 mL) was added and the resulting mixture was stirred at –78° C. under N$_2$ for 3 h. The mixture was stirred for an additional 3 h at room temperature, sat. ammonium chloride solution was added and the resulting mixture was extracted with successive portions of ethyl acetate. The combined organic layer was dried (Na$_2$SO$_4$), filtered and the filtrate concentrated in vacuo. The residue was purified by MPLC on silica gel using 3% MeOH in CH$_2$Cl$_2$ as an eluent to give the compound 35 as an oil: $^1$HNMR (300 MHz, CDCl$_3$) d 6.91 (m, 4H), 4.59 (m, 1H), 4.30 (d, 1H, J=7.64 Hz), 4.21 (m, 1H), 4.15 (d, 1H, J=7.70 Hz), 3.32 (m, 2H), 3.11 (m, 4H), 2.82 (m, 2H), 2.60 (m, 4H), 2.43 (m, 4H), 1.86 (m, 4H), 1.34 (d, 6H, J=6.05 Hz); MS m/z 418 (MH+). The activity of compound 35 in the α1a, α1b and α1c screens was 28, >10000 and 253 nm respectively.

Example 36

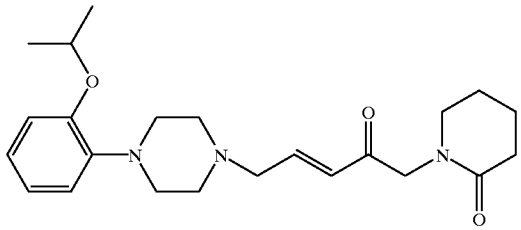

Cpd. 36

Methanesulfonyl chloride (62.7 mM, 0.8 mmol), triethylamine (0.2 mL, 1.1 mmol) and DMAP (3.3 mg, 0.03 mmol) were added to a solution of compound 35 (225 mg, 0.5 mmol) in dichloromethane (15.0 mL) and the mixture was stirred at room temperature under $N_2$ for overnight. The resulting mixture was washed with successive portions of water and the combined organic layer was dried ($Na_2SO_4$), filtered and the filtrate was concentrated in vacuo. The residue was purified by MPLC on silica gel using 3–5% MeOH in $CH_2Cl_2$ to afford compound 36 as oil: $^1$HNMR (300 MHz, $CDCl_3$) d 6.92 (m, 4H), 6.88 (m, 1H), 6.36 ((d, 1H, J=16.1 Hz), 4.61 (m, 1H), 4.39 (s, 2H), 3.30 (bs, 2H), 3.23 (d, 2H, J=4.8 Hz), 3.14 (bs, 4H), 2.66 (bs, 4H), 2.44 (m, 2H), 1.87 (m, 4H), 1.36 (d, 6H, J=6.06 Hz); MS m/z 400 (MH+). The activity of compound 36 in the α1a, α1b and α1c screens was 18, 5316 and 602 nm respectively.

Example 37

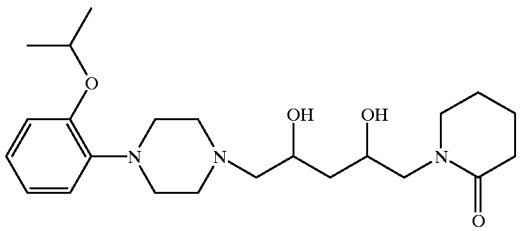

Cpd. 37

Sodium boron hydride (23 mg, 0.6 mmol) was added to a solution of compound 2 (125 mg, 0.3 mmol) in methanol (8.0 mL) at 0° C. under $N_2$ and the mixture was stirred at room temperature for overnight. Solvent was removed under reduced pressure and the residue was dissolved in ethyl acetate and washed with successive portions of water. The combined organic layer was dried ($Na_2SO_4$), filtered and the filtrate was concentrated in vacuo to afford the title compound as a solid without further purification: $^1$HNMR (300 MHz, $CDCl_3$) d 6.91 (m, 4H), 4.59 (m, 1H), 4.14 (m, 1H), 3.57 (m, 1H), 3.42 (m, 4H), 3.13 (bs, 5H), 2.86 (m, 1H), 2.66 (m, 2H), 2.42 (m, 6H), 1.81 (m, 5H), 1.58 (m, 1H), 1.34 (d, 6H, J=6.06 Hz). The activity of compound 37 in the α1a, α1b and α1c screens was 53, >10000 and 224 nm respectively.

BIOLOGICAL EXAMPLES

Biological activity and selectivity of compounds of the invention was demonstrated by the following in vitro assays. The first assay tested the ability of compounds of Formula I to bind to membrane bound receptors α1$_a$-AR, α1$_b$-AR and α1$_d$-AR.

Example 38

The DNA sequences of the three cloned human α1-AR subtypes have been published. Furthermore, the cloned cDNAs have been expressed both transiently in COS cells and stably in a variety of mammalian cell lines (HeLa, LM(tk-), CHO, rat-1 fibroblast) and have been shown to retain radioligand binding activity and the ability to couple to phosphoinositide hydrolysis. We used published DNA sequence information to design primers for use in RT-PCR amplification of each subtype to obtain cloned cDNAs. Human poly A+ RNA was obtained from commercially available sources and included hippocampus and prostate samples, sources which have been cited in the literature. For the primary screen a radio ligand binding assay was used which employed membrane preparations from cells expressing the individual cloned receptor cDNAs. Radiolabeled ligands with binding activity on all three subtypes (non-selective) are commercially available ([125I]-HEAT, [3H]-prazosin).

Each α1 receptor subtype was cloned from poly A+ RNA by the standard method of reverse transcription-polymerase chain reaction (RT-PCR). The following sources of polyA+ RNA were used for the cloning of the α1 receptor subtypes: α1$_a$-AR, human hippocampus and prostate, α1$_b$-AR, human hippocampus, α1$_d$-AR, human hippocampus. The resulting cDNAs were cloned into the pcDNA3 mammalian expression vector (Invitrogen Corp., San Diego, Calif.). Each DNA was sequenced for verification and to detect any possible mutations introduced during the amplification process. Any deviation in sequence from the published consensus for each receptor subtype was corrected by site-directed mutagenesis.

The three α1-AR subtypes (a, b, d) were transfected into COS cells using a standard DEAE-dextran procedure with a chloroquine shock. In this procedure, each tissue culture dish (100 mm) was inoculated with 3.5×10$^6$ cells and transfected with 10 μg of DNA. Approximately 72 hours post-transfection, the cells were harvested and COS membranes were prepared. Transfected COS cells from 25 plates (100 mm) were scraped and suspended in 15 mL of TE buffer (50 mM Tris-HCl, 5 mM EDTA, pH7.4). The suspension was disrupted with a homogenizer. It was then centrifuged at 100×g for 10 minutes at 4° C. The supernatant was centrifuged at 34,500×g for 20 minutes at 4° C. The pellet was resuspended in 5 mL TNE buffer (50 mM Tris-HCl, 5 mM EDTA, 150 mM NaCl, pH7.4). The resulting membrane preparation was aliquoted and stored at −70° C. The protein concentration was determined following membrane solubilization with TritonX-100.

The ability of each compound to bind to each of the α1-AR subtypes was assessed in a receptor binding assay. [125I]-HEAT, a non-selective α1-AR ligand, was used as the radiolabeled ligand. Each well of a 96-well plate received: 140 μL TNE, 25 μL [125I]-HEAT diluted in TNE (50,000 cpm; final concentration 50 pM), 10 μL test compound diluted in DMSO (final concentration 1 pM–10 μM), 25 mL COS cell membrane preparation expressing one of the three α1-AR subtypes (0.05–0.2 mg membrane protein). The plate was incubated for 1 hour at room temperature and the reaction mixtures were filtered through a Packard GF/C Unifilter filter plate. The filter plate was dried for 1 hour in a vacuum oven. Scintillation fluid (25 mL) was added to each well, and the filter plate was counted in a Packard Topcount scintillation counter. Data was analyzed using GraphPad Prism software.

Tables A–J list the $IC_{50}$ values expressed in nanomolar concentration for select compounds of the invention in all receptor subtypes.

TABLE A

| Cpd# | $R_1$ | $R_2$ | $R_3$ | $R_4$ | B | Z | α1a | α1b | α1d | Scheme |
|---|---|---|---|---|---|---|---|---|---|---|
| 3 | H | i-propyl | H | H | O | $(CH_2)_3$ | 2.1 | 3915 | 177 | 1 |
| 33 | H | i-propyl | H | $CH_3$ | O | $(CH_2)_3$ | 8.8 | 642 | 130 | 1 |

TABLE B

| Cpd# | $R_1$ | $R_2$ | $R_3$ | B | Z | α1a | α1b | α1d | Scheme |
|---|---|---|---|---|---|---|---|---|---|
| 4 | H | i-propyl | H | O | $(CH_2)_3$ | 79 | >10000 | >10000 | 1 |

TABLE C

| Cpd# | $R_1$ | $R_2$ | $R_3$ | B | Z | α1a | α1b | α1d | Scheme |
|---|---|---|---|---|---|---|---|---|---|
| 12 | H | i-propyl | H | O | $(CH_2)_3$ | 4643 | >10000 | >10000 | 3 |
| 34 | H | i-propyl | H | O | $(CH_2)_2$ | 2957 | >10000 | >10000 | 3 |
| 35 | H | i-propyl | H | O | $(CH_2)_4$ | 6933 | >10000 | >10000 | 3 |
| 51 | H | i-propyl | O | O | IID* | 163 | >10000 | >8385 | 3 |
| 52 | H | i-propyl | O | O | CPDA** | 595 | >10000 | >8285 | 3 |

*IID is 1H-isoindole-1,3(2H)dion-1-yl
**CPDA is 1,1-cyclopentanediacetimid-1-yl

TABLE D

| Cpd# | R₁ | R₂ | R₃ | B | Z | α1a | α1b | α1d | Scheme |
|---|---|---|---|---|---|---|---|---|---|
| 28 | H | i-propyl | H | O | (CH₂)₂ | 2.2 | >5985 | 131 | 7 |
| 36 | H | i-propyl | H | O | (CH₂)₃ | 6.3 | >10000 | 215 | 7 |
| 37 | H | phenyl | H | O | (CH₂)₃ | 56 | >10000 | 69 | 7 |
| 38 | H | phenyl | H | O | (CH₂)₂ | 30 | 4410 | 341 | 7 |
| 39 | H | phenyl | H | O | (CH₂)₄ | 172 | >10000 | 570 | 7 |

TABLE E

| Cpd# | R₁ | R₂ | R₃ | B | Z | α1a | α1b | α1d | Scheme |
|---|---|---|---|---|---|---|---|---|---|
| 54 | H | CH₃ | H | O | (CH₂)₃ | 1732 | 3022 | 500 | 4 |
| 41 | H | CH₃ | H | O | CH₂ | 7628 | 3167 | 1684 | 4 |
| 42 | H | CH₃ | H | O | (CH₂)₄ | 8589 | 1419 | 526 | 4 |
| 43 | H | CH₃ | H | O | (CH₂)₂ | 7723 | 2644 | 1565 | 4 |
| 44 | H | CH₃ | H | O | (CH₂)₅ | 2030 | 3937 | 577 | 4 |
| 19 | H | i-propyl | H | O | (CH₂)₂ | 258 | 12360 | 454 | 4 |
| 45 | H | i-propyl | O | O | (CH₂)₃ | 98 | 96 | 197 | 4 |
| 46 | H | i-propyl | O | O | (CH₂)₂ | 69 | 1753 | 174 | 4 |
| 47 | H | i-propyl | Ph | O | (CH₂)₃ | 147 | 3318 | 291 | 4 |
| 53 | H | i-propyl | O | O | CPDA | 147 | 3318 | 291 | 4 |

TABLE F

| Cpd# | R₁ | R₂ | R₃ | B | Z | α1a | α1b | α1d | Scheme |
|---|---|---|---|---|---|---|---|---|---|
| 8 | H | i-propyl | H | O | (CH₂)₃ | 3.8 | 4.456 | 272 | 2 |

TABLE G

| Cpd# | R₁ | R₂ | R₃ | B | Z | α1a | α1b | α1d | Scheme |
|---|---|---|---|---|---|---|---|---|---|
| 9 | H | i-propyl | H | O | (CH₂)₃ | 89 | 10000 | 1517 | 2 |

TABLE H

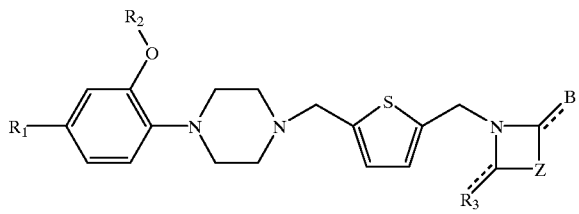

| Cpd# | $R_1$ | $R_2$ | $R_3$ | B | Z | α1a | α1b | α1d | Scheme |
|---|---|---|---|---|---|---|---|---|---|
| 23 | H | $CH_3$ | H | O | $(CH_2)_2$ | 80 | >1000 | 46 | 5 |
| 24 | H | $CH_3$ | $CO_2Et$ | H | $(CH_2)_2$ | 23 | 1188 | 30 | 6 |
| 48 | H | $CH_3$ | H | O | $(CH_2)_3$ | 29 | >10000 | 26 | 5 |
| 49 | H | $CH_3$ | H | O | $(CH_2)_4$ | 37 | >10000 | 24 | 5 |
| 50 | H | $CH_3$ | $CH_2OH$ | H | $(CH_2)_3$ | 838 | >5139 | 261 | 6 |

TABLE I

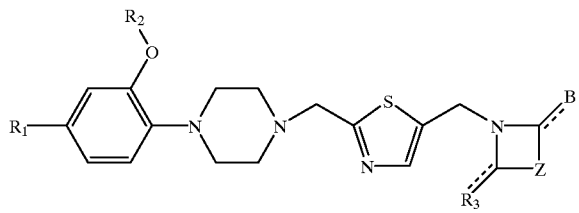

| Cpd# | $R_1$ | $R_2$ | $R_3$ | B | Z | α1a | α1b | α1d | Scheme |
|---|---|---|---|---|---|---|---|---|---|
| 16 | H | i-propyl | H | O | $(CH_2)_3$ | 1.88 | 8502 | 211 | 3 |
| 17 | H | i-propyl | H | O | $(CH_2)_2$ | 2.5 | 3470 | 79 | 3 |

TABLE J

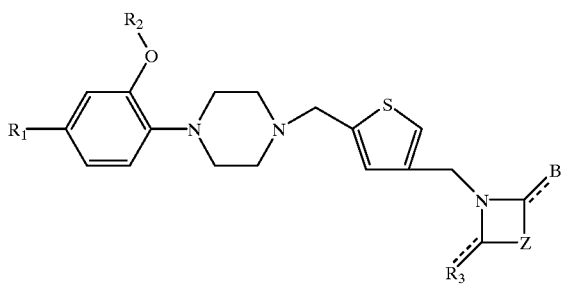

| Cpd# | $R_1$ | $R_2$ | $R_3$ | B | Z | α1a | α1b | α1d | Scheme |
|---|---|---|---|---|---|---|---|---|---|
| 32 | H | i-propyl | H | O | $(CH_2)_2$ | 0.83 | 620 | 24 | 8 |
| 55 | H | i-propyl | H | O | $(CH_2)_3$ | 1.0 | 768 | 185 | 8 |
| 56 | H | i-propyl | H | O | $(CH_2)_4$ | 3.7 | 1230 | 95 | 8 |

Example 39

The antagonist activity and the selectivity of compounds of the invention for prostate tissues over aortic tissues as well as their antagonists was demonstrated as follows. The contractile responses of rat prostatic tissue and rat aorta tissues were examined in the presence and absence of antagonist compounds. As an indication of the selectivity of antagonism, test compound effects on vascular smooth muscle contractility ($α1_b$-AR and $α1_d$-AR) were compared to the effects on prostatic smooth muscle ($α1_a$-AR). Strips of prostatic tissue and aortic rings were obtained from Long Evans derived male rats weighing 275 grams and sacrificed by cervical dislocation. The prostate tissue was placed under 1 gram tension in a 10 ml bath containing phosphate buffered saline pH 7.4 at 32° C. and isometric tension was measured with force transducers. The aortic tissue was placed under 2 grams tension in a 10 ml bath containing phosphate buffered saline pH 7.4 at 37° C. The ability of test compound to reduce the norepinephrine-induced contractile response by 50% ($IC_{50}$) was determined. Compound 3 inhibited the contractile response in aortic tissue with an $IC_{50}$ of 31.9 μM and in prostate tissue with an $IC_{50}$ of 1.3 μM. Compound 16 inhibited the contractile response in aortic tissue with an $IC_{50}$ of 13.5 μM and in prostate tissue with an $IC_{50}$ of 0.38 μM.

Example 40

Compound 3 was tested for its ability to antagonize phenylephrine (PE) induced increases in intraurethral pressure in dogs. The selectivity of the compound was demonstrated by comparing their effect upon PE induced increases in mean arterial pressure (MAP) in the dog.

Male beagle dogs were anesthetized and catheterized to measure intraurethral pressure (IUP) in the prostatic urethra. Mean arterial pressure (MAP) was measured using a catheter placed in the femoral artery. Dogs were initially administered six i.v. bolus doses (1 to ≦32 mg/kg) of phenylephrine (PE) to establish a control agonist dose-response curve. IUP and MAP were recorded following each dose until the IUP returned to baseline. The dogs then were given an i.v. bolus dose of the antagonist compound, followed by i.v. PE challenges of ascending doses, as in the control agonist dose-response curve. IUP and MAP measurements following each PE challenge were recorded. The antagonist compound was tested over a dose range of 3 to 300 ug/kg in half-log increments. The interval between antagonist doses was at least 45 minutes and three experiments were performed per dose level for each test compound. The graphs below illustrates the mean percentage reductions in IUP and MAP for compound 3.

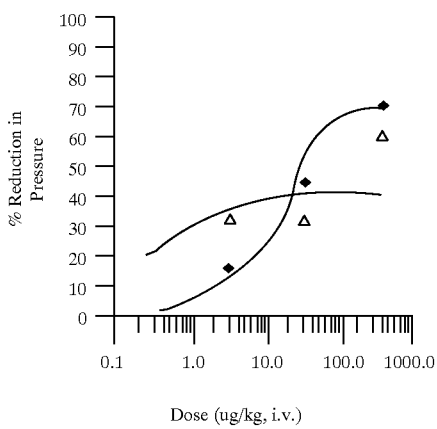

Effects of Compound 3 upon IUP and MAP at 10 μg/kg PE Dogs

REFERENCES

Breslin D, Fields D W, Chou T-C, Marion D N, Kane M, Vaughan E D, and Felsen D (1993) Investigative urology: medical management of benign prostatic hyperplasia: a canine model comparing the in vivo efficacy of alpha-1 adrenergic antagonists in the prostate. J. Urol. 149: 395–399.

Bruno J F, Whittaker J, Song J, and Berelowitz M. (1991) Molecuar cloning and sequencing of a cDNA encoding a human α1A adrenergic receptor. Biochem. Biophys. Res. Commun. 179: 1485–1490.

Bylund D B, Eikenberg D C, Hieble J P, Langer S Z, Lefkowitz R J, Minneman K P, Molinoff P B, Ruffolo R R, and Trendelenburg U (1994) IV. International Union of Pharmacology nomenclature of adrenoceptors. Pharmacol. Rev. 46: 121–136.

Carruthers S G (1994) Adverse effects of α1-adrenergic blocking drugs. Drug Safety 11: 12–20.

Faure C, Gouhier C, Langer S Z, and Graham D (1995) Quantification of α1-adrenoceptor subtypes in human tissues by competitive RT-PCR analysis. Biochem. Biophys. Res. Commun. 213: 935–943.

Flavahan N A and VanHoutte P M (1986) α-Adrenoceptor classification in vascular smooth muscle. Trends Pharmacol. Sci. 7: 347–349.

Ford A P D W, Arredondo N F, Blue D R, Bonhaus D W, Jasper J Dava M S, Lesnick J, Pfister J R, Shieh I A, Vimont R L, Williams R J, McNeal J E, Stamey T A, and Clarke D E (1996) R S-17053 (N-[2-(2-Cyclopropylmethoxyphenoxy)ethyl]-5-chloro-a,a-dimethyl-1H-indole-3-ethanamine hydrochloride), a selective α1a-adrenoceptor antagonist, displays low affinity for functional α1-adrenoceptors in human prostate: Implications for adrenoceptor classification. Mol. Pharmacol. 49: 209–215.

Forray C, Bard J A, Wegzel J M, Chiu G, Shapiro E, Tang R, Lepor H, Hartig P R, Weinshank R L, Branchek T A, and Gluchowski C (1994) The α1-adrenergic receptor that mediates smooth muscle contraction in human prostate has the pharmacological properties of the cloned human α1c subtype. Mol. Pharmacol. 45: 703–708.

Gormley G, Stoner E, Bruskewitz R C et al. (1992) The effects of finasteride in men with benign prostatic hyperplasia. N. Engl. J. Med. 327: 1185–1191.

Hatano A Takahashi H, Tamaki M, Komeyama T, Koizumi T, and Takeda M (1994) Pharmacological evidence of distinct α1-adrenoceptor subtypes mediating the contraction of humanprostatic urethra and peripheral artery. Br. J. Pharmacol. 113: 723–728.

Harrison J K, Pearson W R, and Lynch K R (1991) Molecular characterization of α1- and α1-adrenoceptors. Trends Pharmacol. Sci. 12: 62–67.

Hieble J P and Caine M (1986) Etiology of benign prostatic hyperplasia and approaches to pharmacological management. Fed. Proc. 45: 2601.

Hirasawa A, Horie K, Tanaka T, Takagaki K, Murai M, Yano J, and Tsujimoto G (1993) Cloning, functional expression and tissue distribution of human cDNA for the α1c-adrenergic receptor. Biochem. Biophys. Res. Commun. 195: 902–909.

Holck C M, Jones C H M, and Haeusler G (1983) Differential interactions of clonidine and methoxamine with postsynaptic α-adrenoceptors of rabbit main pulmonary artery. Cardiovasc. Res. 5: 240–248.

Lepor H and Rigaud G (1990) The efficacy of transurethral resection of the prostate in men with moderate symptoms of prostatism. J. Urol. 143: 533–537.

Lepor H, Auerbach S, Puras-Baez A et al. (1992) A randomized, placebo-controlled multi-center study of the efficacy and safety of terazosin in the treatment of benign prostatic hyperplasia. J. Urol. 148: 1467–1474.

Lepor H (1995) α-Blockade for benign prostatic hyperplasia (BPH) J. Clin. Endocrinol. Metab. 80: 750–753.

Marshall I, Burt R P, Andersson P O, Chapple C R, Greengrass P M, Johnson G I, and Wyllie M G (1992) Human α1c-adrenoceptor: functional characterisation in prostate. Br. J. Pharmacol. 112: 59P. Marshall I, Burt R P, and Chapple C R (1995) Noradrenaline contraction of human prostate by α1A-(α1C-)adrenoceptor subtype. Br. J. Pharmacol. 115: 781–786.

Mebust W K, Holtgrewe H L, Cockett A T K, and Peters P C (1989) Transurethral prostatectomy: immediate and postoperative complication: a cooperative study of 13 participating institutions evaluating 3,885 patients J. Urol., 141: 243–247.

Minneman K P, Han C and Abel P W (1988) Comparison of α1-adrenergic receptor subtypes distinguished by chloroethylclonidine and WB4101. Mol. Pharmacol. 33: 509–514.

Minneman K P and Esbenshade T A (1994) α1-Adrenergic receptor subtypes. Annu. Rev. Pharmacol. Toxicol. 34: 117–133.

Morrow A L and Creese I (1986) Characterization of alpha 1-adrenergic receptor subtypes in rat brain: A reevaluation of [3H]WB4101 and [3H]prazosin binding. Mol. Pharmacol. 29: 321–330.

Muramatsu I (1992) A pharmacological perspective of α1-adrenoceptors: subclassification and functional aspects, in α-Adrenoceptors (Fujiwara M, Sugimoto T, and Kogure K, eds.). Excerpta Medica Ltd., Tokyo, 193–202.

Muramatsu I, Oshita M, Ohmura T, Kigoshi S, Akino H, Gobara M, and Okada K (1994) Pharmacological characterization of α1-adrenoceptor subtypes in the human prostate: functional and binding studies. Br. J. Urol. 74: 572–577.

Oesterling J E (1995) Benign prostatic hyperplasia. Medical and minimally invasive treatment options. N. Engl. J. Med. 332: 99–109.

Price D T, Lefkowitz R J, Caron M G, Berkowitz D, and Schwinn D A (1994) Localization of mRNA for three distince α1-adrenergic receptor subtypes in human tissues: implications for human α-adrenergic physiology. Mol. Pharmacol. 45: 171–175.

Ramarao C S, Kincade Denker J M, Perez D M, Gaivin R J, Riek R P, and Graham R M (1992) Genomic organization and expression of the human α1B-adrenergic receptor. J. Biol. Chem. 267: 21936–21945.

Schwinn D A, Johnston G I, Page S O, Mosley M J, Wilson K H, Worman N P, Campbell S, Fidock M D, Furness L M, Parry-Smith D J, Peter B, and Bailey D S (1995) Cloning and pharmacological characterization of human alpha-1 adrenergic receptors: sequence corrections and direct comparison with other species homologues. JPET 272: 134–142.

Weinberg D H, Trivedi P, Tan C P, Mitra S, Perkins-Barrow A, Borkowski D, Strader C D, and Bayne M (1994) Cloning, expression and characterization of human α adrenergic receptors α1A, α1B, and α1C. Biochem. Biophys. Res. Commun. 201: 1296–1304.

Weis K A, Epstein R S, Huse D M, Deverka P A and Oster G (1993) The costs of prostatectomy for benign prostatic hyperplasia. Prostate 22: 325–334.

Wennberg J E, Roos N, Sola L, Schori A, and Jaffe R (1987) Use of claims data systems to evaluate health care outcomes: mortality and reoperation following prostatectomy. JAMA 257: 933–936.

Yamada S, Tanaka C, Kimura R, and Kawabe K (1994) Alpha 1-adrenoceptors in human prostate: characterization and binding characteristics of alpha 1-antagonists. Life Sci. 54: 1845–1854.

What is claimed is:

1. A compound of Formula I

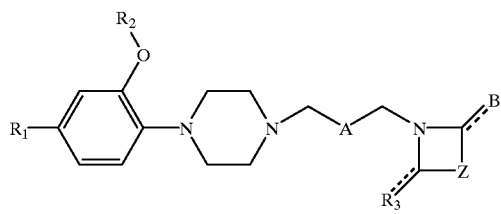

wherein:

$R_1$ is hydrogen, halogen, $C_{1-5}$alkoxy, hydroxyl, or $C_{1-6}$alkyl;

$R_2$ is $C_{1-6}$alkyl, substituted $C_{1-6}$alkyl
where the alkyl substituents are one or more halogens, phenyl, substituted phenyl
where the phenyl substituents are independently selected from one or more of the group consisting of $C_{1-5}$alkyl, $C_{1-5}$alkoxy, and trihalo$C_{1-5}$alkyl), phenyl$C_{1-5}$alkyl, or substituted phenyl$C_{1-5}$alkyl
where the phenyl substituents are independently selected from one or more of the group consisting of $C_{1-5}$alkyl, halogen, $C_{1-5}$alkoxy, and trihalo$C_{1-5}$alkyl;

$R_3$ is hydrogen, $C_{1-5}$alkoxycarbonyl, $C_{1-5}$alkyl, hydroxy$C_{1-5}$alkyl, formyl, acetyl, amido, or oxygen
where if $R_3$ is oxygen the hashed line is solid is taken together with the other solid line to represent a double bond, and if $R_3$ is not oxygen, the hashed line represents a single bond affixed to a hydrogen;

A is selected from the group consisting of

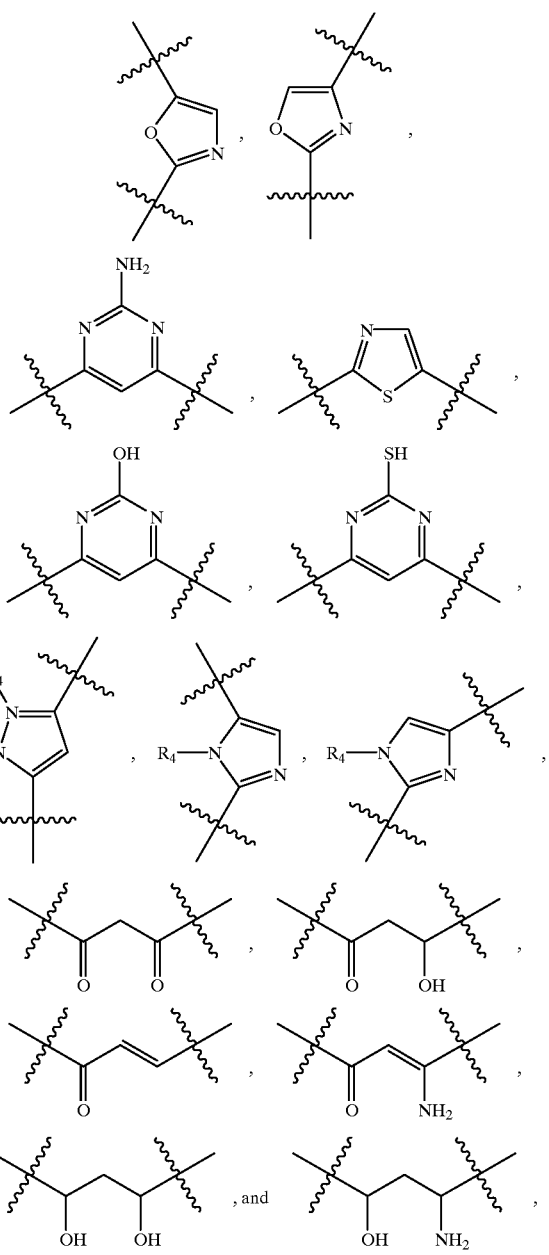

where the points of attachment are depicted by the hashed bonds,
where one point of attachment is bonded to the methylene adjacent to the depicted piperazine and the second point of attachment is bonded to the other methylene;

$R_4$ is hydrogen or $C_{1-5}$alkyl;

B is hydrogen or oxygen,
where if B is oxygen the hashed line is solid and is taken together with the other solid line to represent a double bond, and if B is hydrogen the hashed line represents a single bond affixed to a hydrogen;

z is —(CH$_2$)n— where n is 1–5, —CH$_2$—CR$_5$R$_6$—CH$_2$—, —CHR$_5$R$_6$CH—
where $R_5$ and $R_6$ are hydrogen, $C_{1-5}$alkyl or taken together to form a $C_{3-8}$cycloalkane,

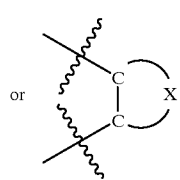

where ring X is an aromatic ring of 6 members;
or pharmaceutically acceptable salts thereof.

2. The compounds of claim 1 where $R_1$ is hydrogen or $C_{1-6}$alkyl, Z is $(CH_2)_n$, n is 1–4 and A is

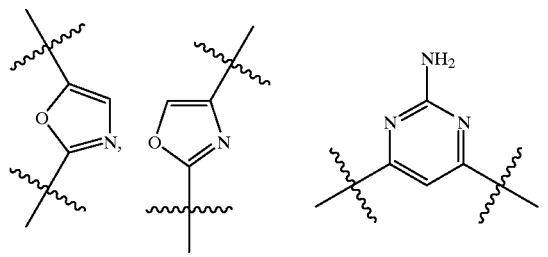

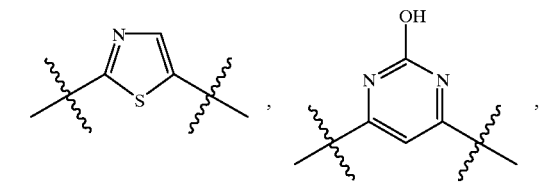

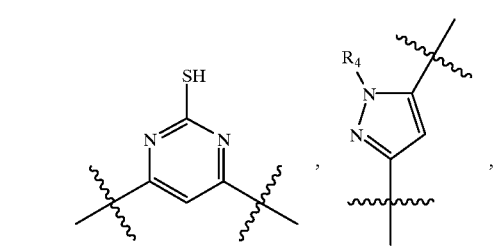

3. The compounds of claim 2 where A is

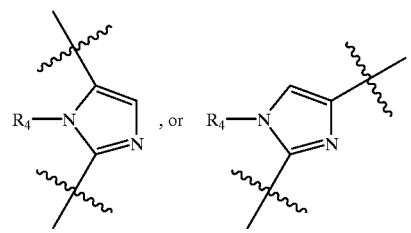

-continued

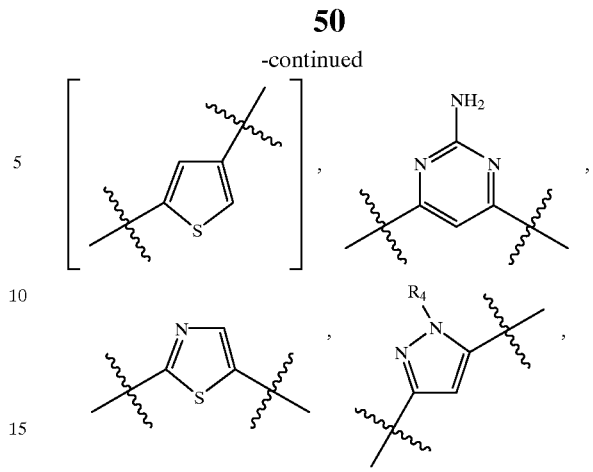

4. The compounds of claim 1 where $R_1$ is hydrogen, $R_2$ is $C_{1-6}$alkyl, phenyl or substituted phenyl, $R_3$ is hydrogen, $R_4$ is hydrogen, B is oxygen, Z is $(CH_2)_n$, n is 1–4, and A is

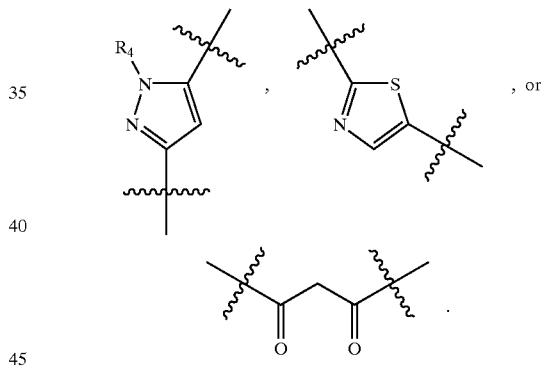

5. A compound and pharmaceutically acceptable salts thereof selected from the group consisting of

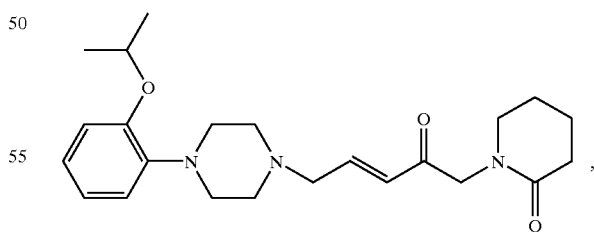

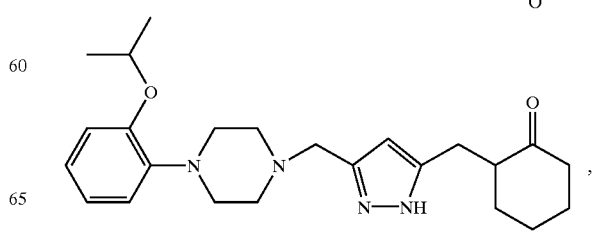

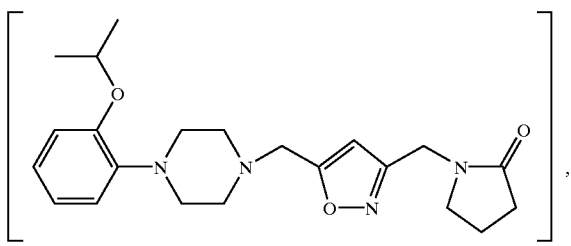,
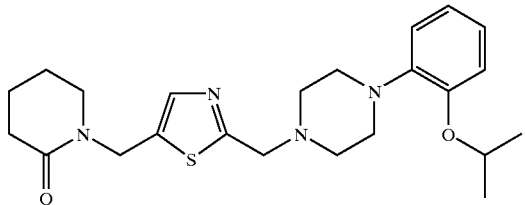,
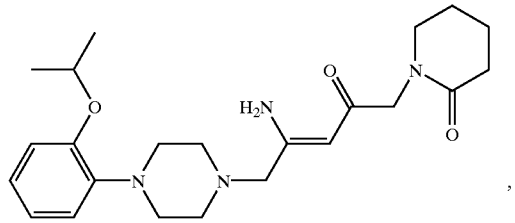,
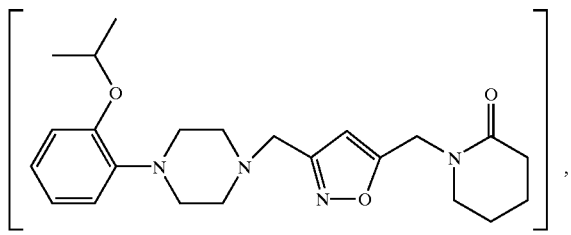,
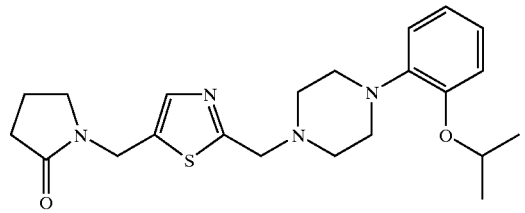,
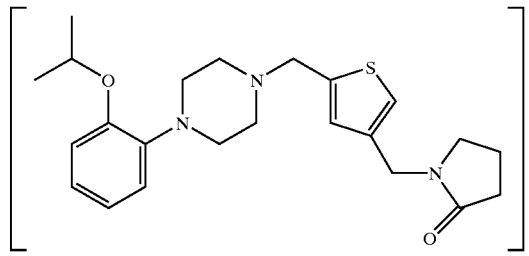,
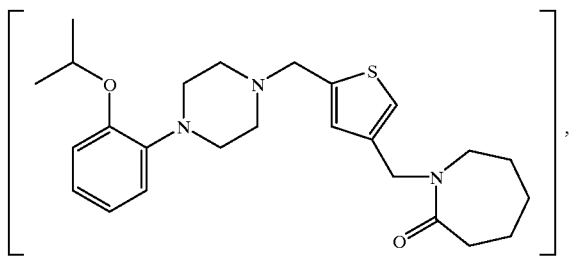
and
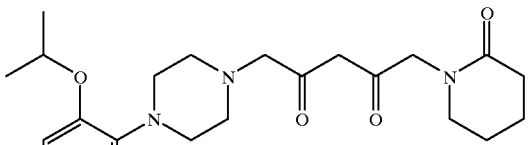,
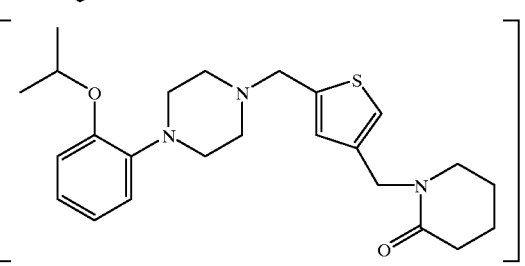.
6. A pharmaceutical composition comprising a compound according to claim 1 and a pharmaceutically acceptable carrier or diluent.
7. The pharmaceutical composition of claim 6 comprising a pharmaceutically acceptable carrier or diluent, and a compound selected from the group consisting of
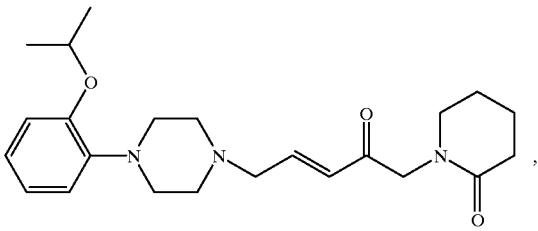,
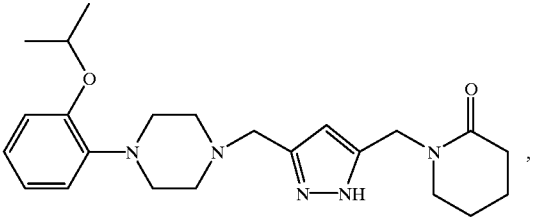,
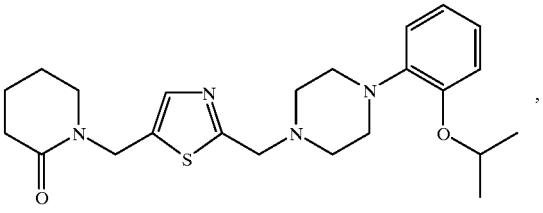,
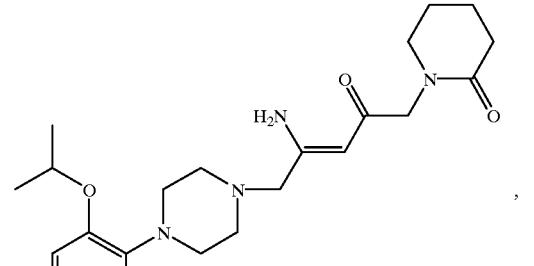,

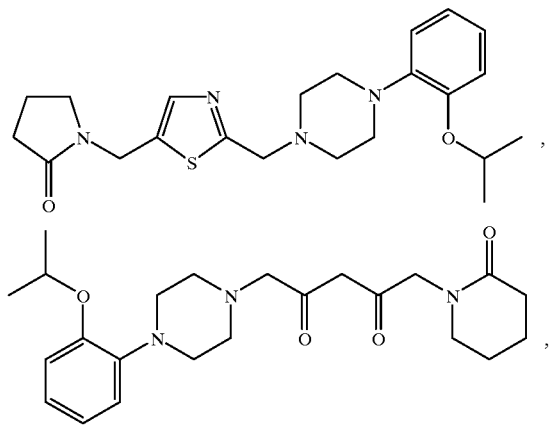

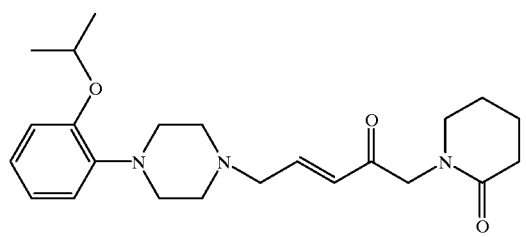

and pharmaceutically acceptable salts thereof.

8. A method of treating a disease mediated by the α-1$_a$ adrenergic receptor comprising administering a compound of claim 1 to a patient at an effective dose.

9. The method of claim 8 comprising administering to a patient an effective dose of a compound selected from the group consisting of

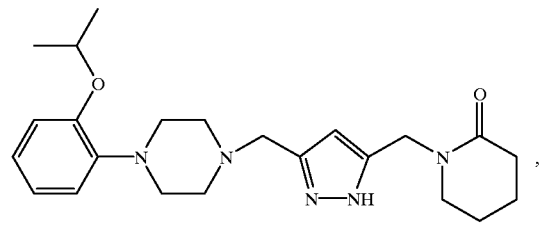

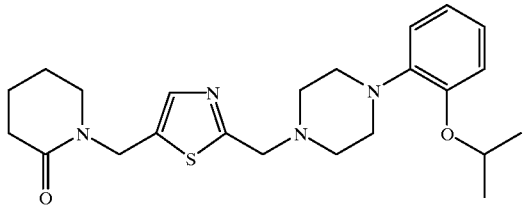

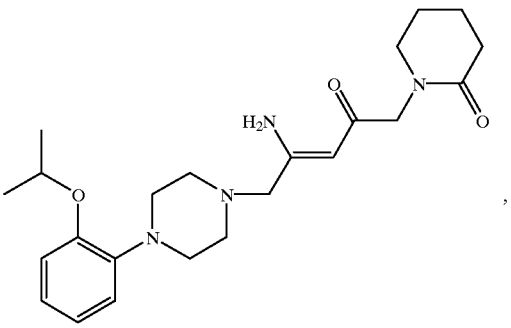

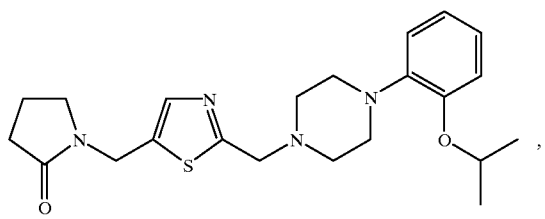

and pharmaceutically acceptable salts thereof.

10. The method of claim 8 where the compound is administered orally and an effective dose is 0.01–100 mg/kg daily.

11. The method of claim 8 where the dose is 0.05–1.0 mg/kg daily.

12. A method of treating benign prostatic hyperplasia comprising administering an effective dose of a compound of claim 1.

* * * * *